(12) United States Patent
Latov et al.

(10) Patent No.: US 9,375,473 B2
(45) Date of Patent: Jun. 28, 2016

(54) METHOD TO TREAT AUTOIMMUNE DEMYELINATING DISEASES AND OTHER AUTOIMMUNE OR INFLAMMATORY DISEASES

(75) Inventors: Norman Latov, Irvington, NY (US); Grace Lee, Riverdale, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 13/579,019

(22) PCT Filed: Feb. 18, 2011

(86) PCT No.: PCT/US2011/025387
§ 371 (c)(1),
(2), (4) Date: Nov. 29, 2012

(87) PCT Pub. No.: WO2011/103389
PCT Pub. Date: Aug. 25, 2011

(65) Prior Publication Data
US 2013/0108643 A1    May 2, 2013

Related U.S. Application Data

(60) Provisional application No. 61/306,043, filed on Feb. 19, 2010.

(51) Int. Cl.
*A61K 39/00* (2006.01)
*C07K 16/28* (2006.01)
*A61K 39/395* (2006.01)

(52) U.S. Cl.
CPC ............. *A61K 39/3955* (2013.01); *C07K 16/28* (2013.01); *C07K 16/2896* (2013.01); *A61K 2039/505* (2013.01); *C07K 2317/34* (2013.01); *C07K 2317/55* (2013.01)

(58) Field of Classification Search
CPC ............................. A61K 31/715; A01N 43/04
See application file for complete search history.

(56) References Cited

U.S. PATENT DOCUMENTS

| | | | |
|---|---|---|---|
| 5,194,596 A * | 3/1993 | Tischer et al. | 530/399 |
| 5,350,836 A * | 9/1994 | Kopchick et al. | 530/399 |
| 8,017,113 B2 | 9/2011 | Karin | |
| 8,133,875 B2 | 3/2012 | Wang et al. | |
| 8,409,569 B2 | 4/2013 | Karin | |
| 8,486,396 B2 | 7/2013 | Karin et al. | |
| 2006/0035834 A1* | 2/2006 | Karin | 514/12 |
| 2006/0194237 A1 | 8/2006 | Latov et al. | |

(Continued)

FOREIGN PATENT DOCUMENTS

| CN | 101292162 A | 10/2008 |
|---|---|---|
| CN | 101305021 A | 11/2008 |

(Continued)

OTHER PUBLICATIONS

Gough, et al., (J Lipid Res. Mar. 1998; 39(3):531-43).*

(Continued)

*Primary Examiner* — Cherie M Stanfield
(74) *Attorney, Agent, or Firm* — Schwegman Lundberg & Woessner, P.A.

(57) ABSTRACT

The invention relates to methods of preventing or inhibiting the onset and/or treating autoimmune demyelinating neuropathy and other autoimmune or inflammatory diseases involving macrophage infiltration.

25 Claims, 3 Drawing Sheets

(56) References Cited

U.S. PATENT DOCUMENTS

| | | | |
|---|---|---|---|
| 2006/0194238 A1* | 8/2006 | Latov et al. | 435/6 |
| 2007/0059242 A1* | 3/2007 | Wentworth | 424/9.1 |
| 2008/0242618 A1 | 10/2008 | Khan et al. | |
| 2008/0254072 A1* | 10/2008 | Wang et al. | 424/278.1 |
| 2009/0275064 A1 | 11/2009 | Wentworth | |
| 2010/0003711 A1 | 1/2010 | Wentworth | |

FOREIGN PATENT DOCUMENTS

| | | |
|---|---|---|
| CN | 101675066 A | 3/2010 |
| CN | 102844050 A | 12/2012 |
| EP | 1602931 A1 | 12/2005 |
| WO | WO-2007/031996 A1 | 3/2007 |
| WO | WO-2007/115045 A2 | 10/2007 |
| WO | WO-2009/039337 A2 | 3/2009 |
| WO | WO-2011103339 | 8/2011 |
| WO | WO-2011103389 | 8/2011 |

OTHER PUBLICATIONS

UniProt P21757 (MSRE_HUMAN). May 1, 1991.*
"Chinese Application Serial No. 201180019657.7, Office Action mailed Sep. 6, 2013", (w/ English Translation), 17 pgs.
"European Application Serial NO. 11745296.1, Supplementary European Search Report mailed Nov. 15, 2013", 10 pgs.
Bradl, M., et al., "Progressive multiple sclerosis", *Semin Immunopathol.*, 31(4), (Nov. 2009), 455-465.
Lee, G., et al., "Differential gene expression in chronic inflammatory demyelinating polyneuropathy (CIDP) skin biopsies", *J Neurol Sci.*, 290(1-2), (Mar. 15, 2010), 115-122.
Lee, G., et al., "Therapy of Experimental Inflammatory Demyelinating Neuropathy with Anti-MSRI IgG Fab", (Abstract T-83), Annals of Neurology, 68(4), *39th Annual Meeting of the Child Neurology Society*, Providence, RI, USA, (2010), p. S56.
Lee, J. G. et al., "A combination of Lox-1 and Nox1 regulates TLR9-mediated foam cell formation", *Cell Signal.*, 20(12), (Dec. 2008), 2266-2275.
Renaud, S., et al., "Gene expression profiling in chronic inflammatory demyelinating polyneuropathy", *J Neuroimmunol.*, 159(1-2), (Feb. 2005), 203-14.
"International Application Serial No. PCT/US2011/025387, International Preliminary Report on Patentability mailed Aug. 30, 2012", 9 pgs, 2012.
Haasken, S., et al., "Macrophage Scavenger Receptor 1 (Msr1, SR-A) Influences B Cell Autoimmunity by Regulating Soluble Autoantigen Concentration", J Immunol., 191(3), (Aug. 1, 2013), 1055-62.
Wikipedia_MSR1. [online]. [Retrieved on Apr. 11, 2011]. Retrieved from the /en.wikiped ia.org/wiki/MSR1>, for different nam es of MSR1, (Sep. 25, 2010).
"International Application Serial No. PCT/US2011/025387, Search Report mailed Apr. 26, 2011", 5 Pgs, 2011.
"International Application Serial No. PCT/US2011/025387, Written Opinion mailed Apr. 26, 2011", 7 Pgs, 2011.
Benhar, I., "Design of synthetic antibody libraries", Expert Opin Biol Ther., 7(5), (May 2007), 763-79.
Cihakova, D., et al., "Interleukin-13 protects against experimental autoimmune myocarditis by regulating macrophage differentiation", Am J Pathol., 172(5), (May 2008), 1195-208.
Li, J., et al., "Research and development of next generation of antibody-based therapeutics", Acta Pharmacol Sin., 31(9), (Sep. 2010), 1198-207.
Murdoch, et al., "Hypoxia Regulates Macrophage Functions in Inflammation", J Irnmunol, vol. 175, Abstract; and p. 6259, col. 1, para 2; for inflammato ry disease atherosclerosis, macroph age Infiltration, (2005), p. 6257-6263.
Moore, K. J., et al., "Loss of receptor-mediated lipid uptake via scavenger receptor A or CD36 pathways does not ameliorate atherosclerosis in hyperlipidemic mice", The Journal of Clinical Investigation, 115(8), (2005), 2192-2201.

Picataggi, A., et al., "A coding variant in SR-BI (I179N) significantly increases atherosclerosis in mice", Mamm Genome, 24, (2013), 257-265.
Prabhudas, M., et al., "Standardizing Scavenger Receptor Nomenclature", The Journal of Immunology, 192, (2014), 1997-2006.
Raycroft, M. T., et al., "Inhibition of Antigen Trafficking through Scavenger Receptor A", The Journal of Biological Chemistry, 287(8), (2012), 5310-5316.
"Chinese Application Serial No. 201180019657.7, Response filed Jan. 21, 2014 to Office Action mailed Sep. 6, 2013", (w/ English Translation of Claims), 1-14.
"European Application Serial No. 11745296.1, Office Action mailed Dec. 3, 2013", 1 pg.
Feng, H., et al., "Deficiency of Scavenger Receptor BI Leads to Impaired Lymphocyte Homeotasis and Autoimmune Disorders in Mice", *Arterioscler. Thromb. Vasc. Biol.*, 31, (2011), 2543-2551.
Fraser, I., et al., "Divalent cation-independent macrophage adhesion inhibited by monoclonal antibody to murine scavenger receptor", *Nature*, 364, (1993), 343-346.
Fujita, Y., et al., "C-Reactive Protein Uptake by Macrophage Cell Line via Class-A Scavenger Receptor", *Clinical Chemistry*, 56:3, (2010), 478-481.
Gowen, B. B., et al., "The collagenous domain of class A scavenger receptors is involved in macrophage adhesion to collagens", *Journal of Leukocyte Biology*, 69, (2001), 575-582.
Józefowski, S., et al., "Disparate Regulation and Function of the Class A Scavenger Receptors SR-AI/II and MARCO", *J. Immunol.*, 175, (2005), 8032-8041.
Józefowski, S., et al., "The class A scavenger receptor SR-A/CD204 and the class B scavenger receptor CD36 regulate immune functions of macrophages differently", *Innate Immunity*, (2013), 1-22.
Levy-Barazany, Hilit, et al., "Expression of Scavenger receptor A on antigen presenting cells is important for CD4[30] T-cells proliferation in EAE mouse model", *Journal of Neuroinflammation*, 9:120, (2012), 1-8.
Yi, H., et al., "Targeting the Immunoregulator SRA/CD204 Potentiates Specific Dendritic Cell Vaccine-Induced T-cell Response and Antitumor Immunity", *Cancer Research*, 71, (2011), 6611-6620.
"Chinese Application Serial No. 201180019657.7, Office Action mailed Nov. 3, 2014", (w/ English Translation), 17 pgs.
"Chinese Application Serial No. 201180019657.7, Response filed Jul. 4, 2014 to Office Action mailed Apr. 22, 2014", (w/ English Translation of Claims), 18 pgs.
"Chinese Application Serial No. 201180019657.7, Response filed Jan. 19, 2015 to Office Action mailed Nov. 3, 2014", (w/ English Translation of Amended Claims), 14 pgs.
"Canadian Application Serial No. 2,790,203, Preliminary Amendment filed Aug. 17, 2012", 13 pgs.
"Chinese Application Serial No. 201180019657.7, Office Action mailed May 25, 2015", (w/ English Translation), 13 pgs.
"Chinese Application Serial No. 201180019657.7, Response filed Aug. 10, 2015 to Office Action mailed May 25, 2015", (w/ English Translation of Claims), 14 pgs.
"European Application Serial No. 11745296.1, Office Action mailed Mar. 19, 2015", 7 pgs.
"European Application Serial No. 11745296.1, Response filed Jul. 3, 2015 to Office Action mailed Mar. 9, 2015", 11 pgs.
"Chinese Application Serial No. 201180019657.7, Office Action mailed Apr. 22, 2014", With English Translation, 14 pgs.
"European Application Serial No. 11745296.1, Response filed May 23, 2014 to Office Action mailed Dec. 3, 2013", 13 pgs.
Hyam, Supriya R., et al., "Arctigenin ameliorates inflammation in vitro and in vivo by inhibiting the PI3K/AKT pathway and polarizing M1 macrophages to M2-like macrophages", European Journal of Pharmacology, vol. 708, Issues 1-3, (May 15, 2013), 21-29.
"Chinese Application Serial No. 201180019657.7, Decision of Rejection mailed Dec. 11, 2015", (w/ English Translation), 14 pgs.

* cited by examiner

*FIG. 3A* *FIG. 3B*
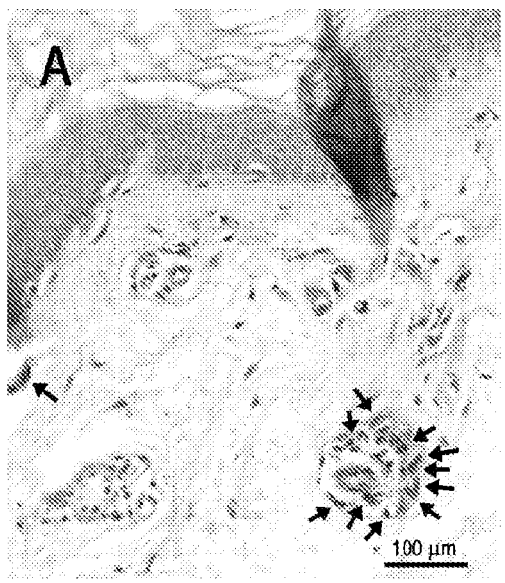 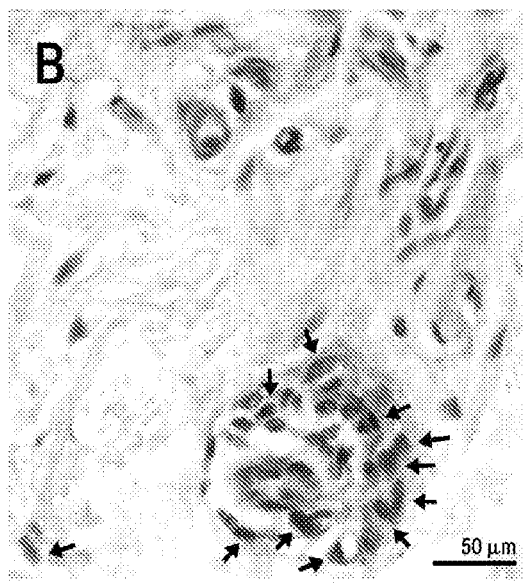
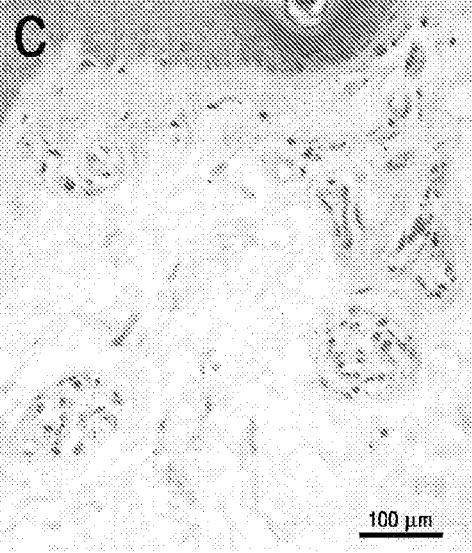 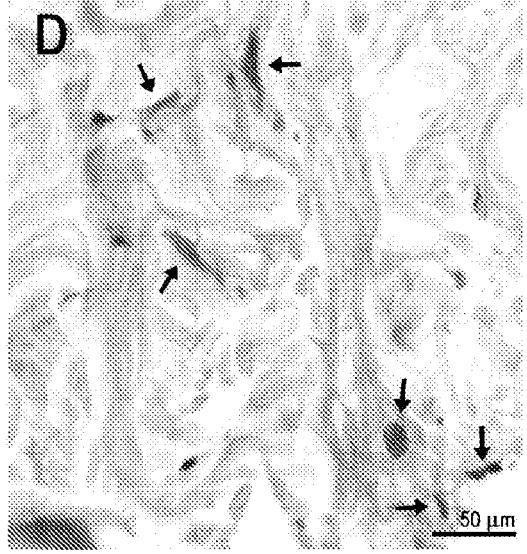
*FIG. 3C* *FIG. 3D*

METHOD TO TREAT AUTOIMMUNE DEMYELINATING DISEASES AND OTHER AUTOIMMUNE OR INFLAMMATORY DISEASES

RELATED APPLICATIONS

This application is a nationalization under 35 U.S.C. 371 of PCT/US2011/025387, filed Feb. 18, 2011, published as WO 2011/103389, publication date Aug. 25 2011, which claims the benefit of priority, under 35 U.S.C Section 119(e) to U.S. patent application Ser. No. 61/306,043, filed Feb. 19, 2010; which applications are incorporated herein by reference in their entirety.

BACKGROUND

Autoimmune polyneuropathies arise when nerves are damaged by the body's own immune system. Symptoms of these diseases include numbness, muscle weakness, limb pain, cramping, sensitivity to touch and reduced tendon reflex. In general, autoimmune polyneuropathies can be categorized into demyelinating and axonal neuropathies.

One type of demyelinating neuropathy is chronic inflammatory demyelinating polyneuropathy (CIDP). The prevalence of CIDP is about 9 persons per 100,000 (Laughlin et al, *Neurology* 73:39 (2009)). However, the prevalence of all types of demyelinating neuropathies is about 20 per 100,000. Another type of demyelinating neuropathy is acute inflammatory demyelinating polyneuropathy (AIDP, Guillain-Barre Syndrome), which has an incidence of 2-3 per 100,000 per year. At least one type of neuropathy is associated with the presence of antibodies directed against myelin-associated glycoprotein (MAG) antibodies.

Autoimmune axonal neuropathies include vasculitic neuropathy, sensory ganglioneuritis (Sjogren's syndrome and other collagen vascular diseases), autoimmune autonomic neuropathy, non-length dependent small fiber neuropathy and paraneoplastic neuropathy.

Corticosteroids and/or immunosuppressants have been used to treat these types of autoimmune neuropathies but new therapies may be more effective when targeted to specific biological molecules that contribute to the development of the neuropathies.

SUMMARY

The present invention is directed to a method of inhibiting autoimmune demyelinating neuropathy and other autoimmune or inflammatory diseases involving macrophage infiltration in a mammal in need thereof. This method involves administering to the mammal with such a disease an inhibitor that binds to macrophage scavenger receptor class 1 (MSR1) under conditions effective to inhibit the development of such autoimmune or inflammatory diseases. In one embodiment of this invention, the inhibitor is a Fab fragment of an antibody to MSR1. Such antibodies can be monoclonal or polyclonal or a functional portion thereof. The mammals can be rabbits, rats, mice, horses, cows, goats, primates or humans, preferably human.

One aspect of the invention is a method of treating an autoimmune or inflammatory disease in a mammal comprising: administering to a mammal in need thereof an inhibitor of MSR1 under conditions effective to inhibit an autoimmune or inflammatory disease, wherein the disease comprises macrophage infiltration. Examples of inhibitors of MSR1 include an anti-MSR1 antibody, an anti-MSR1 antibody fragment, a Fab fragment of an anti-MSR1 antibody, an F(ab)$_2$ fragment of an anti-MSR1 antibody, and/or any functional equivalents of these antibodies and antibody fragments. In some embodiments, a combination of inhibitors of MSR1 is employed.

When the inhibitor is an antibody, it can be any type of antibody. For example, the antibody can be a monoclonal antibody, and/or the antibody fragment or the Fab fragment can be obtained from a monoclonal antibody. In other embodiments, the antibody is a polyclonal antibody and/or the antibody fragment or the Fab fragment is obtained from a polyclonal antibody preparation.

In some embodiments, the antibody, the antibody fragment or the Fab fragment of an anti-MSR1 antibody is from a recombinant antibody library. Recombinant antibodies, antibody fragments and/or Fab fragments can be expressed in eukaryotic cells (e.g., mammalian or yeast cells) or prokaryotic cells (e.g., bacteria). The antibody, the antibody fragment and/or the Fab fragment of an anti-MSR1 antibody can also be generated through an in vitro technique. For example, a library of antibodies, antibody fragments or Fab fragments of an anti-MSR1 antibody can be generated, obtained or employed, where the antibodies, antibody fragments or Fab fragments are displayed on phage, cells or ribosomes.

The antibody, antibody fragment, Fab fragment or the functional equivalent thereof can bind to any MSR1 polypeptide or peptide, including any mammalian MSR1. For example, the mammalian MSR1 polypeptides and peptides to which the antibodies, antibody fragments, Fab fragments or functional equivalents thereof can bind include human, rat, mouse, goat, horse, dog, cat or avian MSR1. In some embodiments, the antibody, antibody fragment, Fab fragment or the functional equivalent thereof can bind to any of SEQ ID NO:1-9.

The mammal treated by the methods described herein can be a human or a domesticated or zoo animal.

In some embodiments, the disease is an autoimmune disease, including any of the autoimmune diseases disclosed herein. For example, the autoimmune disease can be an autoimmune demyelinating neuropathy such as chronic inflammatory demyelinating polyneuropathy (CIDP) or Guillain-Barre syndrome (GBS). In other embodiments, the disease is an inflammatory disease, including any of the inflammatory diseases disclosed herein.

While not being limited to a specific mechanism of action, the inhibitor of MSR1 can for example, deactivate previously activated macrophages, inhibit macrophage activation, inhibit macrophage interactions, inhibit antigen presentation, and/or inhibit extracellular adhesion in the mammal.

The conditions effective to inhibit an autoimmune or inflammatory disease can include administration of a therapeutically effective amount of the inhibitor of MSR1. Such a therapeutically effective amount of the inhibitor of MSR1 can deactivate previously activated macrophages, inhibit macrophage activation, inhibit macrophage interactions, inhibit antigen presentation and/or inhibit extracellular adhesion. In some embodiments, the therapeutically effective amount of the inhibitor of MSR1 reduces inflammation, reduces demyelination, reduces axonal loss and/or reduces neuronal loss in the mammal.

Conditions effective for inhibiting the onset or duration of an autoimmune or inflammatory disease can also include administering the inhibitor of MSR1 at dosing intervals effective for treating the disease or inhibiting the onset of the disease. For example, in some embodiments the inhibitor is administered once, twice or three times per day. In other embodiments, the inhibitor is administered once, twice or three times per week, or once, twice or three times per month.

BRIEF DESCRIPTION OF THE DRAWINGS

To further investigate the role of MSR1 and AIF-1 in the disease pathogenesis, the inventor has generated Fab antibody fragments to MSR1 and AIF-1, and examined their effects on Experimental Autoimmune Neuritis (EAN) in the rat. EAN is an experimental animal model of human autoimmune demyelinating neuropathy. The Fab antibody fragments to MSR1 and AIF-1 were administered to rats after induction of EAN.

FIG. 3. An anti-MSR1 Fab antibody raised against a rat MSR1 peptide cross reacts with human cells, as shown in human skin biopsy paraffin sections immunostained with anti-rat MSR1 Fab fragments. FIG. 3A (200×), 3B and 3D (400×) show human skin biopsy paraffin sections immunostained with anti-MSR1 Fab fragments that were used in the EAN study described above for FIGS. 1 and 2. FIG. 3C (200×) shows a serial section stained with normal goat IgG Fab antibody (negative control).

DETAILED DESCRIPTION OF THE INVENTION

Figure 1:
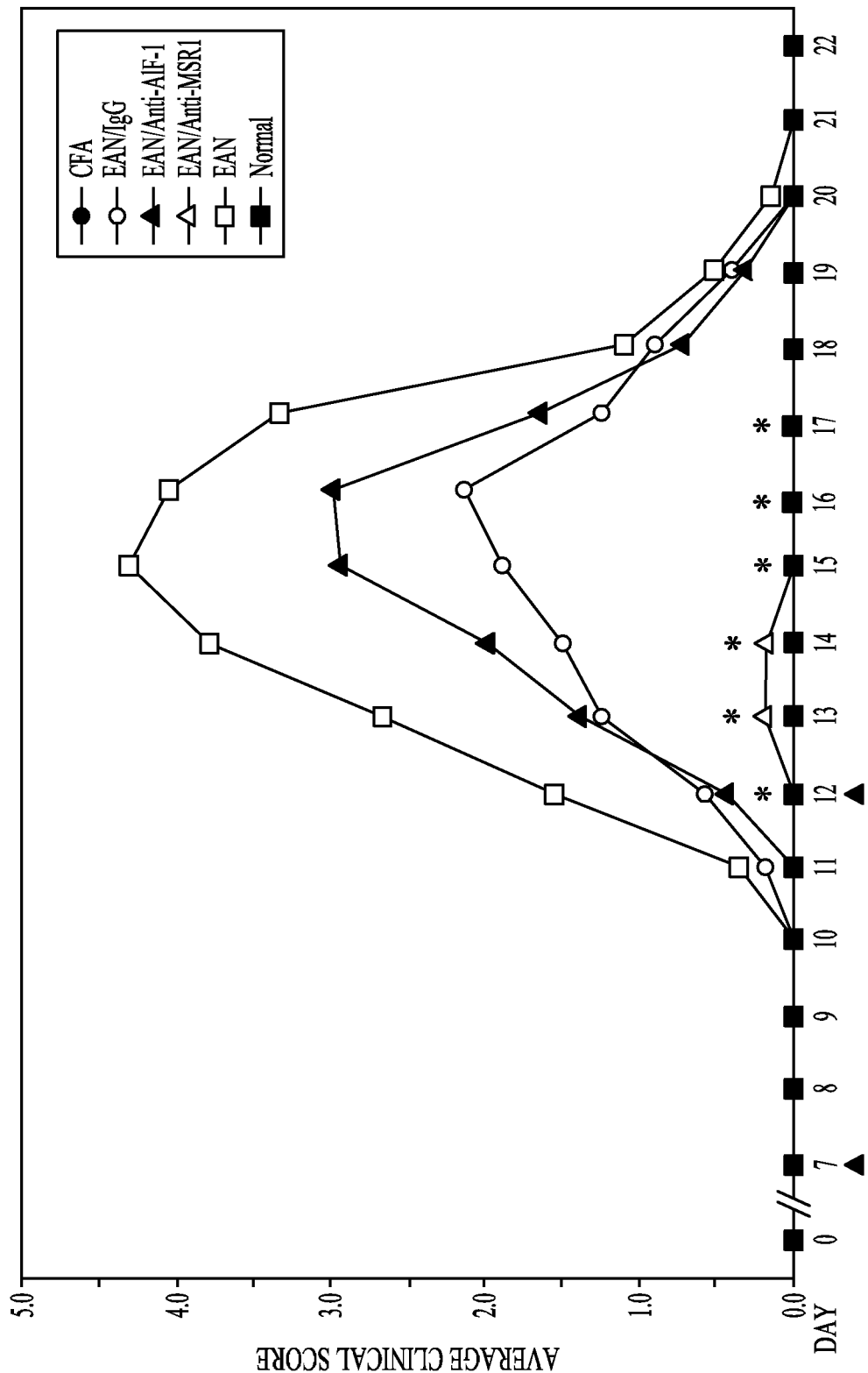
FIG. 1. Effect of treatment with specific and non-specific antibodies on the clinical course of EAN. Animals immunized with P2 peptide in complete Freund's adjuvant (CFA) for induction of EAN were injected intraperitoneally, on days 7 and 12 (arrow heads) with 1 mg of the Fab fragments of IgG specific for MSR1 or AIF-1, or normal goat IgG (Fab) as an isotype control. The average clinical score is shown for each experimental group. Differences in disease severity between untreated EAN rats and those treated with anti-MSR1 were significant at $p<0.05$ between days 12-17 (*).
Figure 2A:
FIG. 2A/D, untreated EAN (100×/400×)
Figure 2B:
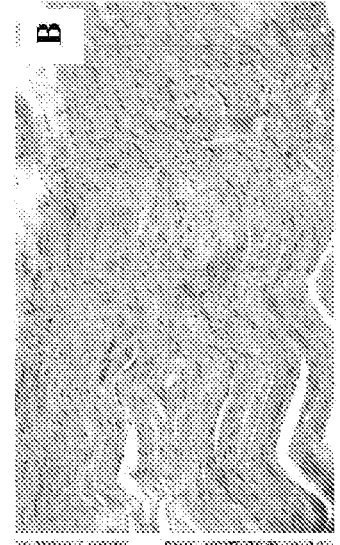
FIG. 2B/E, anti-MSR1 treated EAN (100×/400×)
Figure 2C:
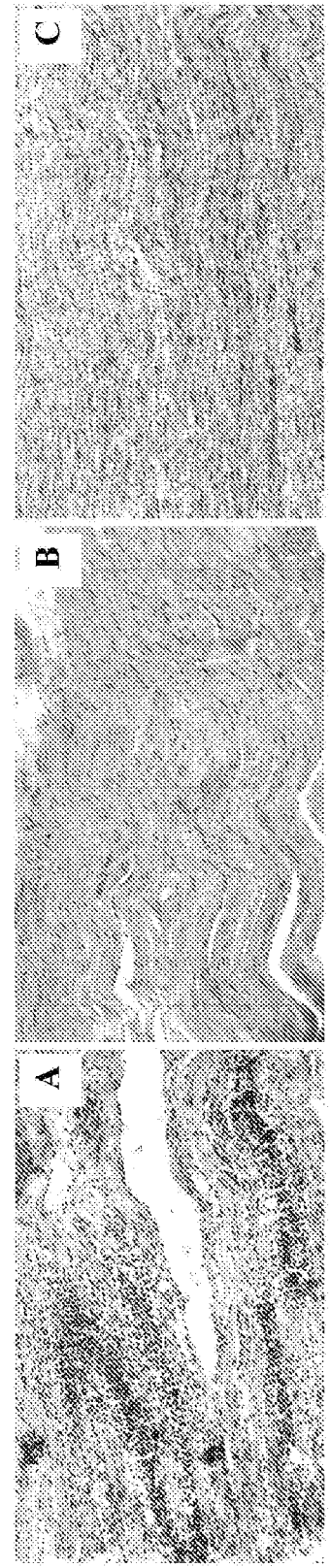
FIG. 2C/F, normal (100×/400×). Representative anti-AIF1 or anti-IgG treated EAN sciatic nerves were similar to untreated EAN and are not shown.
Figure 2D:
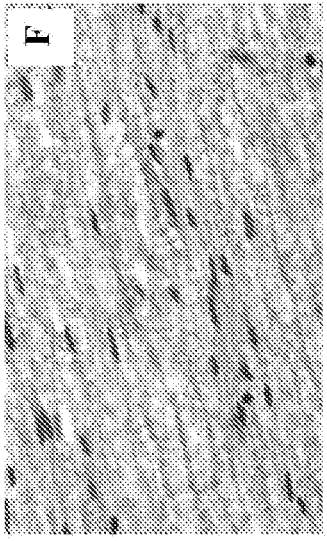
FIG. 2. Fewer inflammatory mononuclear cells infiltrate in anti-MSR1 treated animals than in untreated EAN animals. Hematoxylin and eosin stained paraffin sections of sciatic nerves from representative animals sacrificed at day 17 of disease course.
Figure 2E:
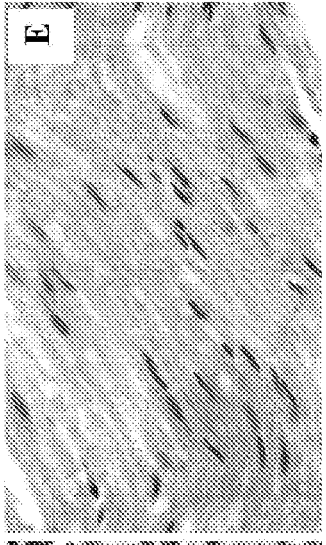
Figure 2F:
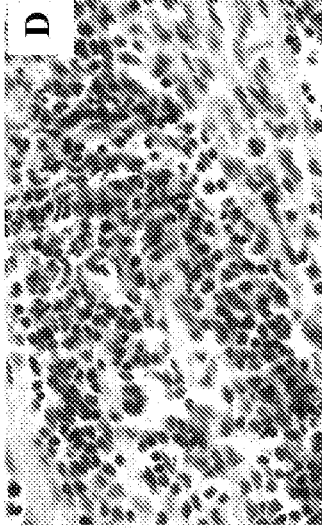

In the following description, reference is made to the accompanying drawings that form a part hereof, and which show by way of illustration specific embodiments that may be practiced. These embodiments are described in detail to enable those skilled in the art to practice the invention, and it is to be understood that other embodiments may be utilized and that structural and logical changes may be made without departing from the scope of the present invention. The following description of example embodiments is, therefore, not to be taken in a limited sense, and the scope of the present invention is defined by the appended claims.

The present invention relates to a method of inhibiting the onset and/or treating the progression of autoimmune and inflammatory diseases in a mammal in need thereof. Autoimmune and inflammatory diseases that can be inhibited or treated by the methods of the invention include those involving macrophage infiltration. In some embodiments, the autoimmune disease is an autoimmune demyelinating neuropathy.

The method involves administering to the mammal an inhibitor of macrophage scavenger receptor class 1 (MSR1) under conditions effective to inhibit the development of autoimmune and/or inflammatory diseases. The mammal can have an autoimmune or inflammatory disease or be predisposed to development of such an autoimmune or inflammatory disease.

As used herein, the inhibitor of MSR1 inhibits the onset, and/or treats, an autoimmune and/or inflammatory disease in a mammal. Thus, the inhibitor is a disease inhibitor and, in some embodiments, the inhibitor may not directly inhibit the function of MSR1. Instead, the inhibitor binds to MSR1 and thereby effectively treats and/or inhibits disease. In other embodiments, the inhibitor does interact with and bind to MSR1 in a manner that inhibits MSR1 function.

In one embodiment of this invention, the inhibitor is an antibody to MSR1 or a Fab fragment thereof. Such antibodies can be monoclonal or polyclonal antibodies, antibody fragments, or functional equivalent of such antibodies and/or fragments.

The mammals can be a human or a domesticated or zoo animal. Examples of mammals in which disease can be inhibited or treated include rabbits, rats, mice, horses, cows, goats, primates or humans. In some embodiments, the mammal is a human.

Macrophage Scavenger Receptor Class 1 (MSR1)

MSR1 is a multi-ligand receptor expressed on macrophages (Usui et al, *Diabetes* 56: 363 (2007); Husemann et al, *Glia* 40: 195 (2002); Platt et al, *J. Clin. Invest.* 108: 649 (2001)). MSR1 is also known as SR-A I/II, CD204, scavenger receptor class A, member 1. It is a transmembrane receptor found on the surface of macrophages, and some mast and dendritic cells. The extracellular collagenous region contains the ligand binding domain.

MSR1 recognizes a variety of endogenous ligands, some of which have been associated with diseases and conditions including antigens, acetylated LDL, β-amyloid, advanced glycation end products, extracellular matrix, and apoptotic cells.

Examples of amino acid sequences for different types and species of MSR1 polypeptides can be found in the art, for example, in the NCBI database. See website at ncbi.nlm.nih.gov. Thus, for example, the NCBI database provides a human Macrophage scavenger receptor class 1 (MSR1) amino acid sequence as accession number P21757.1 (gi: 127357). This sequence is provided below for easy reference as SEQ ID NO:1.

```
  1 MEQWDHFHNQ QEDTDSCSES VKFDARSMTA LLPPNPKNSP

41 SLQEKLKSFK AALIALYLLV FAVLIPLIGI VAAQLLKWET

81 KNCSVSSTNA NDITQSLTGK GNDSEEEMRF QEVFMEHMSN

121 MEKRIQHILD MEANLMDTEH FQNFSMTTDQ RFNDILLQLS

161 TLFSSVQGHG NAIDEISKSL ISLNTTLLDL QLNIENLNGK

201 IQENTFKQQE EISKLEERVY NVSAEIMAMK EEQVHLEQEI

241 KGEVKVLNNI TNDLRLKDWE HSQTLRNITL IQGPPGPPGE

281 KGDRGPTGES GPRGFPGPIG PPGLKGDRGA IGFPGSRGLP

321 GYAGRPGNSG PKGQKGEKGS GNTLTPFTKV RLVGGSGPHE

361 GRVEILHSGQ WGTICDDRWE VRVGQVVCRS LGYPGVQAVH

401 KAAHFGQGTG PIWLNEVFCF GRESSIEECK IRQWGTRACS

441 HSEDAGVTCT L
```

The extracellular domain of this MSR1 polypeptide includes amino acids 77-451 of the SEQ ID NO:1 sequence. This sequence is shown below as SEQ ID NO:2.

```
 77                                KWET

81 KNCSVSSTNA NDITQSLTGK GNDSEEEMRF QEVFMEHMSN

121 MEKRIQHILD MEANLMDTEH FQNFSMTTDQ RFNDILLQLS

161 TLFSSVQGHG NAIDEISKSL ISLNTTLLDL QLNIENLNGK

201 IQENTFKQQE EISKLEERVY NVSAEIMAMK EEQVHLEQEI

241 KGEVKVLNNI TNDLRLKDWE HSQTLRNITL IQGPPGPPGE

281 KGDRGPTGES GPRGFPGPIG PPGLKGDRGA IGFPGSRGLP

321 GYAGRPGNSG PKGQKGEKGS GNTLTPFTKV RLVGGSGPHE

361 GRVEILHSGQ WGTICDDRWE VRVGQVVCRS LGYPGVQAVH

401 KAAHFGQGTG PIWLNEVFCF GRESSIEECK IRQWGTRACS

441 HSEDAGVTCT L
```

As is known to the skilled artisan, sequence variation can be present in human polypeptides, including MSR1 polypeptides. Thus, at least three isoforms of MSR1 exist. These three different isoforms are generated by alternative splicing of this gene. These receptors or isoforms are macrophage-specific trimeric integral membrane glycoproteins. The type 1 and type 2 isoforms are functional receptors and are able to mediate the endocytosis of modified low density lipoproteins (LDLs). The type 3 isoform does not internalize modified LDL (acetyl-LDL) despite having the domain shown to mediate this function in the type 1 and 2 isoforms. It has an altered intracellular processing and is trapped within the endoplasmic reticulum, making it unable to perform endocytosis. The type 3 isoform can inhibit the function of isoform types 1 and 2 when co-expressed, indicating a dominant negative effect and suggesting a mechanism for regulation of scavenger receptor activity in macrophages.

For example, MSR1 types I and II isoform type 1 has an amino acid sequence that is present in the NCBI database as accession number NP_619729.1 (gi: 20357512). This sequence is provided below for easy reference as SEQ ID NO:3.

```
  1 MEQWDHFHNQ QEDTDSCSES VKFDARSMTA LLPPNPKNSP

41 SLQEKLKSFK AALIALYLLV FAVLIPLIGI VAAQLLKWET

81 KNCSVSSTNA NDITQSLTGK GNDSEEEMRF QEVFMEHMSN

121 MEKRIQHILD MEANLMDTEH FQNFSMTTDQ RFNDILLQLS

161 TLFSSVQGHG NAIDEISKSL ISLNTTLLDL QLNIENLNGK

201 IQENTFKQQE EISKLEERVY NVSAEIMAMK EEQVHLEQEI

241 KGEVKVLNNI TNDLRLKDWE HSQTLRNITL IQGPPGPPGE

281 KGDRGPTGES GPRGFPGPIG PPGLKGDRGA IGFPGSRGLP

321 GYAGRPGNSG PKGQKGEKGS GNTLTPFTKV RLVGGSGPHE

361 GRVEILHSGQ WGTICDDRWE VRVGQVVCRS LGYPGVQAVH

401 KAAHFGQGTG PIWLNEVFCF GRESSIEECK IRQWGTRACS

441 HSEDAGVTCT L
```

MSR1 isoform type 2 has an amino acid sequence that is present in the NCBI database as accession number NP_002436.1 (gi:4505259). This sequence is provided below for easy reference as SEQ ID NO:4.

```
  1 MEQWDHFHNQ QEDTDSCSES VKFDARSMTA LLPPNPKNSP

41 SLQEKLKSFK AALIALYLLV FAVLIPLIGI VAAQLLKWET

81 KNCSVSSTNA NDITQSLTGK GNDSEEEMRF QEVFMEHMSN

121 MEKRIQHILD MEANLMDTEH FQNFSMTTDQ RFNDILLQLS

161 TLFSSVQGHG NAIDEISKSL ISLNTTLLDL QLNIENLNGK

201 IQENTFKQQE EISKLEERVY NVSAEIMAMK EEQVHLEQEI

241 KGEVKVLNNI TNDLRLKDWE HSQTLRNITL IQGPPGPPGE

281 KGDRGPTGES GPRGFPGPIG PPGLKGDRGA IGFPGSRGLP

321 GYAGRPGNSG PKGQKGEKGS GNTLRPVQLT DHIRAGPS
```

In addition, in some embodiments it may be useful to administer antibodies directed against MSR1 polypeptides from non-human species. One example of a mouse MSR1 amino acid sequence is one with accession number NP_001106797.1 (gi:164664520). This sequence is provided below for easy reference as SEQ ID NO:5.

```
  1 MTKEMTENQR LCPHEQEDAD CSSESVKFDA RSMTASLPHS

41 TKNGPSLQEK LKSFKAALIA LYLLVFAVLI PVVGIVTAQL

81 LNWEMKNCLV CSLNTSDTSQ GPMEKENTSK VEMRFTIIME

121 HMKDMEERIE SISNSKADLI DTERFQNFSM ATDQRLNDIL

161 LQLNSLISSV QEHGNSLDAI SKSLQSLNMT LLDVQLHTET

201 LNVRVRESTA KQQEDISKLE ERVYKVSAEV QSVKEEQAHV

241 EQEVKQEVRV LNNITNDLRL KDWEHSQTLK NITFIQGPPG

281 PQGEKGDRGL TGQTGPPGAP GIRGIPGVKG DRGQIGFPGG

321 RGNPGAPGKP GRSGSPGPKG QKGEKGSVGG STPLKTVRLV

361 GGSGAHEGRV EIFHQGQWGT ICDDRWDIRA GQVVCRSLGY

401 QEVLAVHKRA HFGQGTGPIW LNEVMCFGRE SSIENCKINQ

441 WGVLSCSHSE DAGVTCTS
```

Other examples of MSR1 polypeptide sequences can be found in the NCBI database. For example, useful MSR1 nucleic acid and polypeptide sequences include those with the following accession numbers:

NM_001191939 (RNA), XP_001065601 (protein);
NM_138715 (RNA), NP_619729 (protein);
NM_002436 (RNA), NP_002436 (protein); and
NM_001113326 (RNA), NP_001106797 (protein).

The polypeptides with these accession numbers can be used to make antigenic peptides useful for making anti-MSR1 antibodies. Examples of antigenic peptides derived from the foregoing polypeptide sequences include the following.

```
Rat MSR1 (SEQ ID NO: 6):
RSGFPGPKGQKGEKGRAG (aa 328-345)

Human MSR1, I (SEQ ID NO: 7):
RPGNSGPKGQKGEKGSGN (aa 325-342)

Human MSR1, II (SEQ ID NO: 8):
RPGNSGPKGQKGEKGSGN (aa 325-342)

Mouse MSR1 (SEQ ID NO: 9):
RSGSPGPKGQKGEKGSVG (aa 332-349)
```

According to the invention, antibodies directed against MSR1 polypeptides, and functional equivalents of such antibodies, are useful for treating autoimmune and inflammatory diseases. Therefore, MSR1 polypeptides and fragments of MSR1 polypeptides, including antigenic fragments of MSR1 and MSR1 epitopes, can be used to generate anti-MSR1 antibodies. Examples of such polypeptides that can be used to generate anti-MSR1 antibodies include those with any of SEQ ID NOs: 1-5. Moreover, MSR1 fragments and antigenic peptides can be used to generate anti-MSR1 antibodies, including any extracellular domain of an MSR1 polypeptide. Examples of MSR1 fragments and antigenic peptides that can be used to generate anti-MSR1 antibodies include those with SEQ ID NO:2, 6, 7, 8 and 9.

Functional equivalents of an antibody that can be used in the methods described herein include chimerized, modified, humanized, recombinant antibodies and/or fragments of such antibodies, chimerized, modified, humanized, and/or recombinant antibodies. A chimerized antibody comprises the variable region of non-human antibody. A humanized antibody comprises the hypervariable region (CDRs) of a non-human antibody. The variable region other than the hypervariable region, e.g. the framework variable region, and the constant region of a humanized antibody are those of a human antibody. The modified antibody can be deimmunized, i.e. rendered less immunogenic compared to an unmodified counterpart to a given species, e.g. human. Human antibodies can be made by many methods known in the art including immunizing transgenic mice that have been transformed with human immunoglobulin genes (Hudson P and Souriau C, *Nature Medicine* 9: 129 (2003)). Recombinant human antibodies can be engineered from phage display or mRNA (ribosome) display libraries by molecular cloning, generation of diversity and increased affinity, and protein expression in in vitro systems (MacCafferty J et al, *Nature* 348:552 (1990); reviewed in Benhar I, *Expert Opin. Biol. Ther.* 7:763 (2007) and Li J and Zhu Z, *Acta Pharmacol. Sin.* 31:1198 (2010)).

The antibodies or functional equivalents of antibodies interact with, e.g. bind to, MSR1 with affinity and/or specificity. In some embodiments, the anti-MSR1 antibodies and/or functional equivalents of such antibodies bind to MSR1 with high affinity and/or high selectivity. For example, the antibody or functional equivalent can bind to human MSR1 with an affinity constant of at least $10^7$ M$^{-1}$. In some embodiments, the antibody or functional equivalent can bind to human MSR1 with an affinity constant between $10^8$ M$^{-1}$ and $10^{10}$ M$^{-1}$ or about $10^9$ M.

In some embodiments, the antibodies or functional equivalents thereof can also interact with, or bind to, the extracellular domain of MSR1 and most preferably the extracellular domain of human MSR1.

In some embodiments, the antibodies or fragments thereof are recombinant or modified anti-MSR1 antibodies chosen from, for example, a chimeric, a humanized, a deimmunized or an in vitro generated antibody or fragment thereof.

For the purposes of this application, suitable variable and hypervariable regions of non-human antibodies may be derived from antibodies produced by any non-human mammal in which monoclonal antibodies are made. Suitable examples of mammals other than humans include, for example, rabbits, rats, mice, horses, goats, llamas or primates. Mice are preferred. The antibodies can be humanized or deimmunized by any of the methods known in the art.

Functional equivalents further include fragments of antibodies that have binding characteristics that are the same as, or are comparable to, those of the whole antibody. Such fragments may, for example, contain one or both Fab fragments of the F(ab')$_2$ fragment. Preferably, the antibody fragments contain all six complementarity determining regions of the whole antibody, although functional fragments containing fewer than all of such regions, such as three, four or five CDRs, are also included.

The preferred fragments are single chain antibodies, or Fv fragments. Single chain antibodies are polypeptides that comprise at least the variable region of the heavy chain of the antibody linked to the variable region of the light chain, with or without an interconnecting linker. Thus, Fv fragment comprises the entire antibody combining site. These chains may be produced in bacteria or in eukaryotic cells.

The antibodies and functional equivalents may be members of any class of immunoglobulins, such as: IgG, IgM, IgA, IgD, or IgE, and the subclasses thereof. The Fab fragments may also be derived from any such class of immunoglobulin, and the functional equivalents may also be equivalents of, or combinations of, any of the above immunoglobulin classes and subclasses.

Antibodies of the present invention are capable of binding to MSR1 and may function to inhibit the activity of such. Such antibodies may have therapeutic potential, particularly in the treatment of autoimmune diseases by inhibiting the function of macrophages.

Antibodies of the present invention may be either monoclonal antibodies or polyclonal antibodies or functional equivalents thereof. Antibodies of the present invention are capable of binding MSR1 and may function to inhibit the activity of such. Such antibodies may have therapeutic potential, particularly in the treatment of autoimmune demyelinating neuropathies or other autoimmune diseases involving macrophage infiltration by inhibiting the function of MSR1.

Monoclonal antibodies can be produced by techniques available in the art. This process involves obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler et al., *Nature* 256: 495 (1975), which is hereby incorporated by reference in its entirety.

Mammalian lymphocytes are immunized by in vivo immunization of the animal (e.g., a mouse) with a full length native antigen or a peptide representing one or more epitopes of the full antigen. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents (Kohler G and Milstein C., *Eur. J. Immunol.* 6: 511 (1976), which is hereby incorporated by reference in its entirety). This immortal cell line, which is preferably murine, but may also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

Monoclonal antibodies can also be obtained by screening a recombinant combinatorial library such as an antibody phage display library. See, for example, PHAGE DISPLAY—A LABORA- TORY MANUAL, Barbas, et al., eds. Cold Spring Harbor Laboratory Press, Cold Spring Harbor, N.Y., 2001; and Kontermann & Dübel, ANTIBODY ENGINEERING, Heidelberg: Springer-Verlag. Berlin, 2001.

Nucleic acids encoding anti-MSR1 antibodies can be derived from an animal immunized with an MSR1 polypeptide, epitope or antigenic peptide by generating an expression library using the RNA of the animal's B cells or plasma cells and then screening for antibody-coding sequences. See, for example, in *Antibodies, A Laboratory Manual* by Harlow and Lane, Cold Spring Harbor Laboratory Press, Cold Spring Harbor, N.Y., 1988, and in *Molecular Cloning, A Laboratory Manual* by Sambrook, et al., Cold Spring Harbor Laboratory Press, Cold Spring Harbor, N.Y. (1989), the disclosures of which are incorporated herein by reference.

Briefly, immune cells sensitized to the specified antigen (such as mononuclear cells) or spleen cells from animal immunized with an MSR1 polypeptide, epitope or antigenic peptide can be used. The cells are processed according to the phage display technology described by Barbas et al., *Proc. Natl. Acad. Sci., USA* 88: 7978-7982 (1991); and in U.S. Pat. Nos. 5,580,717; 5,972,656; 6,113,898; and 6,140,470. The disclosures of these documents are incorporated herein by reference. Total RNA is isolated from cells and the RNA can be processed to obtain the poly-A RNA. After hybridization of an oligo-d(T) primer, the RNA (mRNA) is reverse transcribed to yield the corresponding cDNA. This cDNA is used to isolate nucleic acids encoding antibodies of the invention. The cDNA can be amplified by polymerase chain reaction (PCR) to obtain nucleic acids encoding antibodies of the invention. Selected primers can be used in PCR to isolate nucleic acids encoding polypeptide fragments such as $V_H$, $V_L$, as well as the constant regions.

The cDNA or PCR products can be inserted into a vector, such as a bacteriophage, a phagemid or a plasmid through use of recombinant DNA techniques well-known in the art. See, Sambrook et al. (1989). The vectors containing the cDNA or PCR products can be introduced into bacteria to produce an expression library, the members of which express a polypeptide encoded by the cDNA or PCR product such as a full-length light or heavy chain polypeptide, a single variable chain polypeptide, or a single chain Fab or Fab'.

The procedure also allows for the production of a polypeptide that is fused to a phage coat protein. The library of recombinant phage can be panned as described in the foregoing references and patents to select members of the library that express an antibody that binds specifically to the E2 glycoprotein or the E1E2 complex. The panning may be accomplished by combining the library with an immobilized antigen, removing the phage not bound, and then removing the bound phage.

Host bacterial cells such as *E. coli* or other suitable bacteria can be transfected with members of the phage library that express an antibody that binds to the selected MSR1 polypeptide, epitope or antigen. The resulting bacterial cells can be separated into colonies by serial dilution and plating so that each colony isolated expresses a unique antibody. The phage can also carry a selection marker such as an antibiotic resistance gene so that host bacterial cells expressing an antibody of the invention can be identified by cultivating the host cell library in culture medium containing the antibiotic. Cultures from single colonies can be examined by a binding assay using an MSR1 polypeptide, epitope or antigenic peptide to identify those expressing an antibody having particular immunoreactivity.

Following selection of bacterial colonies that express an antibody having specific immunoreactivities, the nucleic acid sequences coding for the CDR's, framework regions, or variable or constant regions in the selected cultures can be determined using known nucleotide sequencing procedures. Thus, nucleic acids encoding CDR sequences, framework sequences and/or constant regions of an antibody of the invention can be obtained from a phage library.

PCR amplification of Fd and κ regions from the mRNA of the source mononuclear cells may be performed as described by Sastry et al., *Proc. Natl. Acad. Sci. U.S.A.* 86: 5728 (1989) and Barbas et al., PHAGE DISPLAY: A LABORATORY MANUAL. New York: Cold Spring Harbor Laboratory Press (2001). The PCR amplification can be performed with cDNA obtained by the reverse transcription of the mRNA with primers specific for amplification of heavy chain sequences or light chain sequences.

The PCR amplification of messenger RNA (mRNA) isolated from the mononuclear cells with oligonucleotides that incorporate restriction sites into the ends of the amplified product may be used to clone and express heavy chain sequences (e.g., the amplification of the Fd fragment) and κ light chain sequences from B cells. The oligonucleotide primers, which are analogous to those that have been successfully used for amplification of $V_H$ and $V_L$ sequences (see Sastry et al., Proc. Natl. Acad. Sci. U.S.A., 86, 5728 (1989) and Barbas et al., PHAGE DISPLAY: A LABORATORY MANUAL. New York: Cold Spring Harbor Laboratory Press (2001)), may be used for these amplifications. Restriction endonuclease recognition sequences are typically incorporated into these primers to allow for the cloning of the amplified fragment into a suitable vector (i.e. a phagemid or a λ phage) in a predetermined reading frame for expression.

Phage assembly proceeds via an extrusion-like process through the bacterial membrane. For example filamentous phage M13 may be used for this process. This phage has a 406-residue minor phage coat protein (cpIII) which is expressed before extrusion and which accumulates on the inner membrane facing into the periplasm of *E. coli*. The two functional properties of cpIII, infectivity and normal (non-polyphage) morphogenesis have been assigned to roughly the first and second half of the gene. The N-terminal domain of cpIII binds to the F pili, allowing for infection of *E. coli*, whereas the membrane-bound C-terminal domain, P198-S406, serves the morphogenic role of capping the trailing end of the filament according to the vectorial polymerization model.

A phagemid vector may be constructed to fuse the antibody fragment chain such as an Fab, Fab' or an Fd chain with the C-terminal domain of cpIII (see Barbas et al., *Proc. Natl. Acad. Sci. USA*, 88: 7978 (1991)). A flexible five-amino acid tether (GGGGS; SEQ ID NO:13), which lacks an ordered secondary structure, may be juxtaposed between the expressed fragment chain and cpIII domains to minimize interaction. The phagemid vector may also be constructed to include a nucleotide coding for the light chain of a Fab fragment. The cpIII/Fd fragment fusion protein and the light chain protein may be placed under control of separate lac promoter/operator sequences and directed to the periplasmic space by pelB leader sequences for functional assembly on the membrane. Inclusion of the phage F1 intergenic region in the vector allows for packaging of single-stranded phagemid with the aid of helper phage. The use of helper phage superinfection may result in expression of two forms of cpIII. Consequently, normal phage morphogenesis may be perturbed by competition between the cpIII/Fd fragment fusion protein and the native cpIII of the helper phage for incorporation into the virion. The resulting packaged phagemid may carry native cpIII, which is necessary for infection, and the fusion protein including the Fab fragment, which may be displayed for interaction with an antigen and used for selection. Fusion at the C-terminal domain of cpIII is necessitated by the phagemid approach because fusion with the infective N-terminal domain would render the host cell resistant to infection. The result is a phage displaying antibody combining sites ("Phabs"). The antibody combining sites, such as Fab fragments, are displayed on the phage coat. This technique may be used to produce Phabs which display recombinantly produced Fab fragments, such as recombinantly produced Fab fragments that immunoreact with an antigen, on the phage coat of a filamentous phage such as M13.

A phagemid vector (i.e. pComb 3 or pComb3H) which allows the display of antibody Fab fragments on the surface of filamentous phage, has been described (see Barbas et al., *Proc. Natl. Acad. Sci. USA,* 88: 7978 (1991). Xho I and Spe I sites for cloning PCR-amplified heavy-chain Fd sequences are included in pComb 3 and pComb3H. Sac I and Xba I sites are also provided for cloning PCR-amplified antibody light chains. These cloning sites are compatible with known mouse and human PCR primers (see, e.g., Huse et al., *Science* 246: 1275-1281 (1989)). The nucleotide sequences of the pelB leader sequences are recruited from the λ HC2 and λ LC2 constructs described in Huse et al, ibid, with reading frames maintained. Digestion of pComb 3 and pComb3H, encoding a selected Fab, with Spe I and Nhe I permit the removal of the gene III fragment, which includes the nucleotide sequences coding for the antibody Fab fragments. Because Spe I and Nhe I produce compatible cohesive ends, the digested vector may also be religated to yield a phagemid that produces soluble Fab.

Phabs may be produced by overnight infection of phagemid containing cells (e.g., infected *E. coli* XL-1 Blue) yielding typical titers of $10^{11}$ cfu/ml. By using phagemids encoding different antibiotic resistances, ratios of clonally distinct phage may easily be determined by titering on selective plates. In single-pass enrichment experiments, clonally mixed phage may be incubated with an antigen-coated plate. Nonspecific phage will be removed by washing, and bound phage may then be eluted with acid and isolated.

The antibodies or antibody fragments used in the methods of the invention can also be polyclonal antibodies or fragments thereof.

Procedures for raising polyclonal antibodies are also available. Typically, such antibodies can be raised by administering native antigen or a peptide thereof (e.g., a synthetic peptide coupled to a hapten) subcutaneously to an animal. Animals that can be used to generate polyclonal antibodies include, mice, rats, goats, New Zealand white rabbits, horses, monkeys and other animals. In some embodiments, the animal is first bled to obtain pre-immune serum. The antigens can be injected at a convenient volume for the selected animal species. For example, a rabbit can be injected with total volume of about 100 μl per site and several sites (e.g., at six different sites). One example of the injected material would be an emulsion of the antigens with an effective adjuvant such as Freund's complete adjuvant. The animals are bled at about two weeks after the first injection and periodically boosted with the same antigen, for example, for about three times at six week intervals. A sample of serum is then collected about 10 days after each boost. Polyclonal antibodies are then recovered from the serum. Recovery of polyclonal antibodies can be by affinity chromatography using the corresponding antigen to capture the antibody. Ultimately, the animals can be euthanized. For example, rabbits can be euthanized with pentobarbital 150 mg/Kg IV. This and other procedures for raising polyclonal antibodies, including in other species such as goats, are disclosed in Harlow et. al., editors, *Antibodies: A Laboratory Manual* (1988), which is hereby incorporated by reference in its entirety.

Antibodies that are essentially human may be produced in transgenic mammals, especially transgenic mice that are genetically modified to express human antibodies. Methods for making chimeric and humanized antibodies are also known in the art. For example, methods for making chimeric antibodies include those described in U.S. Pat. Nos. 4,816, 397 and 4,816,567, which are hereby incorporated by reference in their entirety. Methods for making humanized antibodies are described in U.S. Pat. No. 5,225,539, which is hereby incorporated by reference in its entirety.

One method for humanization of antibodies is called CDR-grafting. In CDR-grafting, the regions of the mouse antibody that are directly involved in binding to antigen, the complementarity determining region of CDRs, are grafted into human variable regions to create "reshaped human" variable regions. These fully humanized variable regions are then joined to human constant regions to create complete "fully humanized" antibodies.

In order to create fully humanized antibodies that bind well to an antigen, it is advantageous to design the reshaped human variable regions carefully. The human variable regions into which the CDRs will be grafted are carefully selected. A few amino acid changes can be made to various positions within the framework regions (FRs) of the human variable regions.

For example, the reshaped human variable regions may include up to ten amino acid changes in the FRs of the selected human light chain variable region, and as many as twelve amino acid changes in the FRs of the selected human heavy chain variable region. The DNA sequences coding for these reshaped human heavy and light chain variable region genes are joined to DNA sequences coding for the human heavy and light chain constant region genes, preferably γ1 and κ, respectively. The reshaped humanized antibody is then expressed in mammalian cells and its affinity for its target compared with that of the corresponding murine antibody and chimeric antibody.

Methods for selecting the residues of the humanized antibody to be substituted and for making the substitutions are well known in the art. See, for example, Co et al., *Nature* 351:501-502 (1991); Queen et al., *Proc. Natl. Acad. Sci. USA* 86:10029-1003 (1989) and Rodrigues et al., *Int. J. Cancer,* Supplement 7:45-50 (1992), which are hereby incorporated by reference in their entirety. A method for humanizing and reshaping the 225 anti-EGFR monoclonal antibody, as an example, is described by WO 96/40210, which is hereby incorporated by reference in its entirety. This method can be adapted to humanizing and reshaping antibodies against other proteins.

Methods for making single chain antibodies are also known in the art. Some examples include those described by European Patent Application No. 502 812 and Wels et al., *Int. J. Cancer* 60:137-144 (1995), which are hereby incorporated by reference in their entirety. Single chain antibodies may also be prepared by screening phage display libraries.

Other methods for producing the functional equivalents of antibodies are disclosed in WO 93/21319, European Patent Application No. 239 400, WO 89/09622, European Patent Application No. 338 745, U.S. Pat. No. 5,658,570, U.S. Pat. No. 5,693,780, and European Patent Application No. 332 424, which are hereby incorporated by reference in their entirety.

Administering MSR1 Inhibitors

In practicing the methods of the present invention, the administering step is carried out by administering the subject inhibitor (e.g., and antibody or fragment thereof) systemically or locally. A single inhibitor or a combination of inhibitors can be administered. Thus, for example, the inhibitor(s) can be administered orally, intradermally, intramuscularly, intraperitoneally (ip), intravenously, subcutaneously, or intranasally.

The inhibitor(s) of the present invention may be administered alone or with suitable pharmaceutical carriers, and can be in solid or liquid form, such as by use of tablets, capsules, powders, solutions, suspensions, or emulsions. Thus, in some embodiments the inhibitors are provided in a composition, for example, a pharmaceutical composition.

The inhibitors are administered under conditions effective to inhibit an autoimmune or inflammatory disease, which in the context of the therapeutic methods described herein, refers to conditions, such as time, inhibitor amount, inhibitor concentration, and the like, that are within ordinary skill for practitioner to ascertain and vary as needed to optimize treatment and/or inhibition of the onset of the disease.

The inhibitors are typically administered, for example, in an effective amount (e.g., a therapeutically effective amount). Such an effective amount of the inhibitor(s) can, for example, be sufficient to reduce inflammation, to reduce demyelination, or reduce axonal and/or neuronal loss in a mammal. In some embodiments, the effective amount of the inhibitor(s) deactivates previously activated macrophages, inhibits macrophage activation, inhibits antigen presentation and/or inhibits extracellular adhesion in the mammal.

Examples of effective amounts of the inhibitor(s) include inhibitor doses ranging from about 0.005 µg/kg to about 100 mg/kg, or ranging from about 0.01 µg/kg to about 60 mg/kg. Another example of a desirable effective amount of the inhibitor(s) described herein about 0.5 µg to about 750 mg.

The inhibitors can also be administered at intervals effective for the treatment and/or inhibition of disease. In some embodiments, the inhibitor is administered several times a day (e.g., twice or three times per day). In other embodiments, the inhibitor is administered once per day, once every other day, twice per week or once per week. In still other embodiments, the inhibitor is administered twice per month or once per month. The intervals at which the inhibitors are administered can vary depending upon the half-life of the inhibitor. Thus, for example, the half-life of antibody-based inhibitors can range from several minutes for single domain antibodies and scFvs to several weeks for many IgG molecules. However, the half-life of a therapeutic inhibitor, including a therapeutic antibody or antibody fragment, can be modulated to facilitate or optimize treatment and/or inhibition of disease. For example, in some embodiments the half-life of the inhibitor (including an antibody or antibody fragment inhibitor) is modulated by attachment of polyethylene glycol (PEG), IgG or serum albumin. Such attachment is readily performed using methods available in the art.

The autoimmune diseases that are treated or inhibited include demyelinating neuropathies such as chronic inflammatory demyelinating polyneuropathy (CIDP) and Guillain-Barre syndrome (GBS); autoimmune diseases affecting the brain such as multiple sclerosis, neuromyelitis optica, acute demyelinating encephalomyelitis (ADEM); autoimmune diseases of the muscle such as polymyositis and dermatomyositis; autoimmune diseases of the gastro-intestinal tract such as ulcerative colitis, Crohn's disease, primary biliary cirrhosis, primary cholangitis, and chronic active hepatitis, autoimmune diseases of the vascular system, such as vasculitis, temporal arteritis, Churg Strauss syndrome, granulomatous angiitis and Takayasu arteritis; autoimmune diseases of the renal system such as IgA nephropathy, autoimmune nephritis and Goodpasture's syndrome; autoimmune diseases of the joints such as rheumatoid arthritis, ankylosing spondylitis and polymyalgia rheumatica, autoimmune diseases of the skin such as bullous pemphigoid, atopic dermatitis, alopecia greata, psoriasis and pemphigus; autoimmune diseases of the pulmonary system, such as asthma, pulmonary fibrosis, pulmonary hypertension, alveolitis, and sarcoid; autoimmune diseases of the endocrine system such as juvenile diabetes, Addison's disease, Hashimoto's thyroiditis and autoimmune diseases of the hematopoietic system such as aplastic anemia and idiopathic thrombocytopenia; and autoimmune diseases affecting several systems such as: lupus erythematosus, Sjogren's syndrome and Behcet's disease.

Other degenerative/inflammatory diseases for which this method would be effective include diabetic neuropathy, nephropathy, retinopathy resulting from microvasculitis, as well as stroke; amyotrophic lateral sclerosis (ALS); HIV-1 neuropathy or encephalopathy, and Huntington's chorea, in which macrophages have been demonstrated to play a contributory role.

In addition, the following diseases can be associated with increased MSR1 antibodies, indicating that they are amenable to the therapy using the methods of the invention: Scleroderma, Multiple organ dysfunction syndrome, Acute coronary syndrome, Alzheimer's disease, and Porphyromonas gingivalis.

The inventor has previously reported elevated expression of MSR1, as well as AIF-1 (allograft inflammatory factor 1), in sural nerves and skin of patients with chronic inflammatory demyelinating polyneuropathy (CIDP) (Renaud et al, *J. Neuroimmunol.* 159: 203 (2005); Lee et al., *J. Neurol. Sci.,* 290: 115 (2010)). CIDP is an autoimmune disease that targets myelin sheaths, specifically in the peripheral nerves, and causes progressive weakness and sensory loss.

In CIDP, sural nerve biopsies show macrophage mediated demyelination (Vital et al., *Ultrastruct. Pathol.* 24: 363 (2000)), increased numbers of activated macrophages or macrophage clusters (Griffin et al, *Ann. Neurol.,* 27: Suppl. S64 (1990); Sommer et al, *Neurology,* 65: 1924 (2005)), and increased expression of Macrophage Scav-enger Receptor 1 (MSR1, SRA I/II, CD204) mRNA (Renaud et al, *J. Neuroimmunol.* 159: 203 (2005)). Macrophages have also been shown to cause demyelinating neuropathy in experimental animals via Fas-ligand-dependent mechanisms (Dace et al, *PLos One,* 22:4e7121 (2009)).

The following non-limiting Examples illustrate aspects of the invention, including some methods used in the development of the invention.

EXAMPLES

In the following description, reference is made to the accompanying figures that form a part hereof, and in which is shown by way of illustration specific embodiments which may be practiced. These embodiments are described in detail to enable those skilled in the art to practice the invention, and it is to be understood that other embodiments may be utilized and that structural and logical changes may be made without departing from the scope of the present invention. The following description of example embodiments is, therefore, not to be taken in a limited sense, and the scope of the present invention is defined by the appended claims.

The present description is further illustrated by the following examples, which should not be construed as limiting in any way. The contents of all cited references (including literature references, issued patents, published patent applications as cited throughout this application) are hereby expressly and specifically incorporated by reference. These examples are directed to inhibiting MSR1 with Fab fragments of anti-MSR1 antibodies but can readily be adapted to other inhibitors of MSR1.

Example 1

Generation of Anti-MSR1 and Anti-AIF-1 Antibodies, Including Fab Fragments Thereof Antibodies to peptide sequences for rat MSR1 (amino acids 328-345: RSGFPGPKGQKGEKGRAG; SEQ ID NO:6) and AIF-1 (amino acids 127-140; KNKEHQKPTGP-PAK; SEQ ID NO:10) (GenScript, NJ) were produced by immunization of goats with 0.5 mg of peptide conjugated to KLH (keyhole limpet hemocyanin) hapten in complete Freund's adjuvant (CFA) (primary injection) or incomplete Freund's adjuvant (3 boosts) (Sigma, Mo.). Both the MSR1 and AIF-1 peptides are rat homologues of human sequences previously used to generate anti-human MSR1 and AIF-1 antibodies. For use as in vivo treatment, antigen-column affinity purified IgG antibodies were digested with papain to obtain Fab fragments and remove Fc. Specific activity of immune serum, purified IgG and Fab was monitored by ELISA (enzyme-linked immunosorbent assay) in peptide coated wells. Protein G-column affinity purified and Fab fragmented naive goat IgG was isolated from normal goat serum as an isotype control.

Example 2

Inhibition of Experimental Autoimmune Neuritis (EAN) by Administration of anti-MSR1Fab Fragments Experimental Autoimmune Neuritis (EAN) was induced in female Lewis rats by subcutaneous tail base immunization with 200 ug of peripheral myelin P2 peptide (amino acids 53-78: TESPFKNTEISFKLGQEFEETTADNR; SEQ ID NO:11) (Genemed Synthesis, TX) in CFA containing *Mycobacterium tuberculosis* $H$37RA (Sigma, Mo.) (Lonigro et al, 2009). On day 7, prior to first appearance of clinical disease, and day 12 post-immunization, EAN rats received 1 mg ip of the IgG Fab fragments of goat anti-MSR1, anti-AIF-1, or naive goat antibodies, or an equal volume of PBS. Other control groups received complete Freund's adjuvant (CFA) only or were untreated, normal rats. Animals were assessed daily for weight and severity of disease until recovery by day 21. Disease severity was assessed by two observers in a blinded fashion on the following scale with half point increments given when clinical signs fall in between categories: 0=normal, 1=reduced tone of tail, hanging tail tip, 2=limp tail, 3=tail paralysis, 4=gait ataxia, 5=mild paraparesis of the hind limbs, 6=moderate paraparesis of hind limbs, 7=severe paraparesis or paraplegia of hind limbs, 8=moderate tetraparesis, 9=moribund, 10=death. Formalin fixed, paraffin embedded sections of sciatic nerves from 3 representative animals of each group were stained with hemotoxylin & eosin to assess inflammatory cell infiltration on day 17, near the peak of disease in untreated EAN rats. The total number of cells in longitudinal sections in 8 fields were counted at 100× magnification in each animal.

Statistically significant differences ($p<0.05$) between treatments were determined by the Mann-Whitney for pair-wise and Kruskal-Wallis for multi-group comparisons, Fisher's exact test, and one-way ANOVA for the clinical scores, incidence of disease, and histological finding, respectively (GraphPad Software, USA).

Results

Eight of nine rats immunized with the P2 peptide (amino acids 53-78: TESPFKNTEISFKLGQEFEETTADNR; SEQ ID NO:12) developed signs of neuropathy at day 11, lasting 4 to 9 days, with an average maximal clinical score of 5.0±3.0. The maximum severity of disease ranged from hind limb weakness to severe tetraparesis.

However, administration of anti-MSR1 Fab reduced the average clinical score to 0.2±0.4 ($p<0.05$). Treatment with Fab fragments of anti-MSR1 antibody prevented the onset of EAN in all but 1 of 6 rats. The one animal in which the EAN developed displayed only a minimal clinical sign of neuropathy (a limp tail tip) lasting just 2 days (Table 1). The incidence of disease in the anti-MSR1 group was therefore significantly reduced ($p<0.05$) from that of the untreated EAN group. The maximum severity of clinical disease (FIG. 1, Table 1) was significantly reduced to 0.2±0.4 in the anti-MSR1 antibody treated group in comparison to the untreated EAN rats where it was 5.0±3.0 ($p<0.05$).

The degree of mononuclear cell infiltration in sciatic nerves (FIG. 2, Table 2) was also significantly reduced between the two groups during the period of peak symptoms, with 382±34 cells/mm$^2$ observed in the untreated EAN group in comparison to 6±5 cells/mm$^2$ in the anti-MSR1 treated group ($p<0.001$).

The clinical scores in the anti-AIF-1 or normal IgG Fab treated groups were 3.2±2.6 and 2.4±3.1, respectively, not significantly different from the untreated EAN rats (FIG. 1). Cellular infiltrates in the anti-AIF-1 or native IgG Fab treated groups were similar to that in untreated EAN. However, disease severity was also somewhat reduced by Fab anti-AIF-1 antibody and normal IgG Fab, but the differences did not reach statistically significance in comparison to untreated EAN animals (Table 1, FIG. 1).

TABLE 1

Clinical Course of EAN and Antibody Treatment

| | Group: | | | | | |
|---|---|---|---|---|---|---|
| | EAN | EAN | EAN | EAN | CFA control | Normal |
| | | Fab antibody treatment: | | | | |
| | none | Normal IgG | anti--AIF1 | anti-MSR1 | none | none |
| Entire experimental group: | | | | | | |
| Incidence of disease[a] | 88.9% (8/9) | 50.0% (4/8) | 77.8% (7/9) | 16.7% (1/6)* | 0.0% (0/10) | 0.0% (0/6) |
| Maximum clinical score[b] | 5.0 ± 2.4 | 2.4 ± 3.1 | 3.2 ± 2.6 | 0.2 ± 0.4** | 0 | 0 |
| Duration (days)[b] | 5.9 ± 3.0 | 2.4 ± 3.2 | 3.6 ± 2.7 | 0.3 ± 0.8** | 0 | 0 |

TABLE 1-continued

Clinical Course of EAN and Antibody Treatment

| | Group: | | | | | |
|---|---|---|---|---|---|---|
| | EAN | EAN | EAN | EAN | CFA control | Normal |
| | | Fab antibody treatment: | | | | |
| | none | Normal IgG | anti-AIF1 | anti-MSR1 | none | none |
| Affected animals only: | | | | | | |
| Day of onset[c] | 11.9 ± 0.8 | 13.8 ± 1.9 | 12.4 ± 0.5 | 13.0 | | |
| Maximum clinical score[c] | 5.6 ± 1.6 | 3.8 ± 3.1 | 4.1 ± 2.1 | 1.0 | | |
| Duration (days)[c] | 6.8 ± 1.7 | 3.8 ± 3.3 | 4.8 ± 1.7 | 2.0 | | |

[a](number of animals with overt disease/total number in group)
[b]average of entire group ± standard deviation
[c]average of only animals showing illness within each group ± standard deviation
*significant difference at $p < 0.05$ (Fisher's exact test) compared to EAN group
**significant difference at $p < 0.01$ (Mann-Whitney test) compared to EAN group

TABLE 2

Inflammatory cell infiltration of sciatic nerves

| Group | Antibody (Fab) treatment | Number of mononuclear cells per mm² [a] |
|---|---|---|
| EAN | none | 382 ± 34 |
| EAN | anti-MSR1 | 6 ± 5 * |
| CFA control | none | 7 ± 3 * |
| Normal | none | 2 ± 1 * |

[a] average of 3 representative animals in each group ± standard deviation
* significant difference at $p < 0.001$ (one-way ANOVA) compared to EAN group.

These data indicate that anti-MSR1 antibodies (or Fab fragments thereof) inhibit the onset or reduce the severity of Experimental Autoimmune Neuritis. The marked suppression of EAN by Fab fragments of anti-MSR1 antibody indicates that this represents a novel therapeutic agent in autoimmune demyelinating peripheral neuropathies, as well as in other autoimmune diseases in which macrophages have a pathogenic role.

Anti-MSR1 antibodies (or Fab) therefore inhibits macrophage activity and prevents inflammatory demyelinating neuropathy in experimental rats. Furthermore, these anti-MSR1 antibodies (or Fab) bind to human MSR1 as well as to rat MSR1 (see Example 3). Thus, these data indicate that anti-MSR1 antibodies (or Fab fragments thereof) can be used to treat human inflammatory diseases that involve macrophages, including CIDP or Guillain-Barre syndrome (GBS).

Example 3

Cross Reaction of Anti-Rat MSR1 Antibody (or Fab Fragments Thereof) with Human MSR1

The anti-MSR1 antibodies described in Example 1 were generated against rat MSR1 for in vivo treatment of the rat model of EAN as described in Example 2. These anti-rat MSR1 antibodies were generated by immunization with the rat MSR1 peptide 325-342 (SEQ ID NO:6), which is homologous to the human MSR1 peptides with SEQ ID NOs:7 and 8.

To determine if these anti-rat MSR1 antibodies (or Fab fragments thereof) also bind to MSR1 on human macrophages, paraffin embedded sections of human skin biopsy were incubated with anti-rat MSR1 Fab antibody used in the EAN study. Binding was detected by incubation with biotinylated rabbit secondary antibody against goat IgG F(ab)2, followed by Vector avidin:biotinylated peroxidase complex (ABC) and the peroxidase color substrate, Nova Red. The sections were counterstained with hematoxylin. Human skin sections were similarly immunohistochemically stained with normal goat IgG Fab antibody fragments as a negative control.

As shown in FIG. 3, the anti-MSR1 antibody (or Fab fragments thereof), which was generated by immunization with the rat MSR1 peptide 325-342 (SEQ ID NO:6), also binds to MSR1 on human macrophages. Positive binding was observed when paraffin sections of human skin biopsy were immunohistochemically stained with this anti-rat MSR1 Fab antibody (FIG. 3A, B, D). No binding was detected with a normal goat IgG Fab antibody, a negative control (FIG. 3C).

REFERENCES

Each of the following documents is specifically incorporated herein by reference in its entirety.

Barbas C F, Kang A S, Lerner A, Benkovic S J. Assembly of combinatorial antibody libraries on phage surfaces: the gene III site. Proc Natl Acad Sci, USA 1991; 88: 7978-7982.

Benhar I. Design of synthetic antibody libraries. Expert Opin Biol Ther 2007; 7: 763-79.

Co M S, Queen C. Humanized antibodies for therapy. Nature 1991; 351: 501-2.

Dace D S, Khan A A, Stark J L, Kelly J, Cross A H, Apte R S. Interleukin-10 overexpression promotes Fas-ligand-dependent chronic macrophage-mediated demyelinating polyneuropathy. PLos One. 2009; 22: 4e7121

Griffin J S, Stoll G, Li C Y, Tyor W, Cornblath D R. Macrophage responses in inflammatory demyelinating neuropathies. Ann Neurol 1990; 27: Suppl:S64-8.

Hudson P J, Souriau C. Engineered antibodies. Nat Med 2003; 9: 129-134.

Huse W D, Sastry L, Iverson S A, Kang A S, Alting-Mees M, Burton D R, Benkovic S J, Lerner R A. Science 1989; 246, 1275-1281.

Husemann J, Loike J D, Anankov R, Febbraio M, Silverstein S C. Scavenger receptors in neurobiology and neuropathology: their role on microglia and other cells of the nervous system. Glia 2002; 40: 195-205.

Kohler G, Milstein C. Continuous cultures of fused cells secreting antibody of predefined specificity. Nature 1975; 256:495-7.

Kohler G, Milstein C. Derivation of specific antibody-producing tissues culture and tumor lines by cell fusion. Eur J Immunol 1976; 6:511-9.

Laughlin R S, Dyck P J, Melton U, Leibson C, Ransom J, Dyck P J. Incidence and prevalence of CIDP and the association of diabetes mellitus. Neurology 2009; 73: 39-45.

Lee G, Xiang Z, Brannagan T H, Chin R L, Latov N. Differential Gene Expression in Chronic Inflammatory Demyelinating Polyneuropathy (CIDP) Skin Biopsies. J Neurol Sci 2010; 290: 115-22.

Li J, Zhu Z. Research and development of next generation of antibody-based therapeutics. Acta Pharmacol Sin 2010; 31: 1198-207.

Lonigro A, Devaux J J. Disruption of neurofascin and gliomedin at nodes of Ranvier precedes demyelination in experimental allergic neuritis. Brain 2009; 132: 260-73.

McCafferty J, Griffiths A D, Winter G, Chiswell D J. Phage antibodies: filamentous phage displaying antibody variable domains. Nature 1990; 348: 552-554.

Platt N, Gordon S. Is the class A macrophage scavenger receptor (SR-A) multifunctional?—The mouse's tale. J Clin Invest 2001; 108: 649-54.

Queen C, Schneider W P, Selick H E, Payne P W, Landolfi N F, Duncan J F, Avdalovic N M, Levitt M, Junghans R P, Waldmann T A. A humanized antibody that binds to the interleukin 2 receptor. Proc Natl Acad Sci USA 1989; 86: 10029-33.

Renaud S, Hays A P, Brannagan T H 3rd, Sander H W, Edgar M, Weimer L H, Olarte M R, Dalakas M C, Xiang Z, Danon M J, Latov N. Gene expression profiling in chronic inflammatory demyelinating polyneuropathy. J Neuroimmunol. 2005; 159: 203-14.

Rodrigues M L, Shalaby M R, Werther W, Presta L, Carter P. Engineering a humanized bispecific F(ab')2 fragment for improved binding to T cells. Int J Cancer Suppl. 1992; 7: 45-50.

Sastry L, Alting-Mees M, Huse W D, Short J M, Sorge J A, Hay B N, Janda K D, Benkovic S J, Lerner R A. Cloning of the immunological repertoire in *Escherichia coli* for generation of monoclonal catalytic antibodies: construction of a heavy chain variable region-specific cDNA library. Proc Natl Acad Sci USA 1989; 86, 5728-32.

Sommer C, Koch S, Lammens M, Gabreels-Feston A, Stoll G, Toyka K V, Macrophage clustering as a diagnostic marker in sural nerve biopsies of patients with CIDP. Neurology 2005; 65: 1924-9.

Usui H K, Shikata K, Sasaki M, Okada S, Matsuda M, Shikata Y, Ogawa D, Kido Y, Nagase R, Yozai K, Ohga S, Tone A, Wada J, Takeya M, Horiuchi S, Kodama T, Makino H. Macrophage scavenger receptor-A-deficient mice are resistant against diabetic nephropathy through amelioration of microinflammation. Diabetes. 2007; 56: 363-72.

Vital C, Vital A, Lagueny A, Ferrer X, Fontan D, Barat M, Gbikpi-Benissan G, Orgogozo J M, Henry P, Brechenmacher C, Bredin A, Desbordes P, Ribiere-Bachelier C, Latinville, D, Julien J, Petry K G. Chronic inflammatory demyelinating polyneuropathy: immunopathological and ultrastructural study of peripheral nerve biopsy in 42 cases. Ultrastruct Pathol 2000; 24: 363-9.

Wels W, Beerli R, Hellmann P, Schmidt M, Marte B M, Kornilova E S, Hekele A, Mendelsohn J, Groner B, Hynes N E. EGF receptor and p185erbB-2-specific single-chain antibody toxins differ in their cell-killing activity on tumor cells expressing both receptor proteins. Int J Cancer 1995; 60: 137-44.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "an antibody" includes a plurality (for example, a solution of antibodies or a series of antibody preparations) of such antibodies, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

The following embodiments are part of the invention.

A. A method of treating an autoimmune or inflammatory disease in a mammal comprising: administering to a mammal in need thereof an inhibitor of MSR1 under conditions effective to inhibit an autoimmune or inflammatory disease, wherein the disease comprises macrophage infiltration.

B. The method of embodiment A, wherein the inhibitor of MSR1 is an anti-MSR1 antibody, an anti-MSR1 antibody fragment, a Fab or F(ab)$^2$ fragment of an anti-MSR1 antibody, a functional equivalent of any of these antibodies or antibody fragments, and combinations thereof.

C. The method of any one the preceding embodiments, wherein the antibody is a monoclonal antibody; or the antibody fragment, the Fab fragment or the F(ab)² fragment is from a monoclonal antibody.

D. The method of embodiment A or B, wherein the antibody is a polyclonal antibody; or the antibody fragment, the Fab fragment or the F(ab)₂ fragment is from a polyclonal antibody preparation.

E. The method of any of the preceding embodiments, wherein the antibody, the antibody fragment, the Fab fragment or the F(ab)₂ fragment is from a recombinant antibody library.

F. The method of any one the preceding embodiments, wherein the antibody, the antibody fragment, the Fab fragment or the F(ab)₂ fragment is expressed in eukaryotic cells.

G. The method of any one the preceding embodiments, wherein the antibody, the antibody fragment, the Fab fragment or the F(ab)₂ fragment is expressed in prokaryotic cells.

H. The method of any one the preceding embodiments, wherein the antibody, the antibody fragment, the Fab fragment or the F(ab)₂ fragment is generated through an in vitro technique.

I. The method of embodiment H, wherein the in vitro technique comprises use of a library of antibodies, antibody fragments, Fab fragments or F(ab)₂ fragments, where the antibodies, antibody fragments, Fab fragments or the F(ab)₂ fragment are displayed on phage, cells or ribosomes.

J. The method of any one the preceding embodiments, wherein the antibody, antibody fragment, Fab fragment, F(ab)₂ fragment or the functional equivalent thereof binds to a polypeptide or a peptide comprising any of SEQ ID NO:1-9, such binding can be specific binding and/or high affinity binding, including binding with any of an affinity constants described herein (for example, an affinity constant of at least $10^7$ $M^{-1}$ or with an affinity constant between $10^8$ $M^{-1}$ and $10^{10}$ $M^{-1}$ or about $10^9$ $M^{-1}$).

K. The method of any one the preceding embodiments, wherein the mammal is human.

L. The method of any one the preceding embodiments, wherein the disease is an autoimmune disease, including any autoimmune disease described herein or known to one of skill in the art.

M. The method of any one the preceding embodiments, wherein the disease is an autoimmune demyelinating neuropathy.

N. The method of any one the preceding embodiments, wherein the disease or the autoimmune demyelinating neuropathy is chronic inflammatory demyelinating polyneuropathy (CIDP) or Guillain-Barre syndrome (GBS).

O. The method of any one of embodiments A-K, wherein the disease is an inflammatory disease, including any inflammatory disease described herein or known to one of skill in the art.

P. The method of any one the preceding embodiments, wherein the inhibitor of MSR1 deactivates previously activated macrophages, inhibits macrophage activation, inhibits macrophage interactions, inhibits antigen presentation, and/or inhibits extracellular adhesion in the mammal.

Q. The method of any one the preceding embodiments, wherein the conditions effective to inhibit an autoimmune or inflammatory disease comprise administering a therapeutically effective amount of the inhibitor of MSR1.

R. The method of embodiment Q, wherein the therapeutically effective amount of the inhibitor of MSR1 deactivates previously activated macrophages, inhibits macrophage activation, inhibits macrophage interactions, inhibits antigen presentation or inhibits extracellular adhesion.

S. The method of embodiment Q or R, wherein the therapeutically effective amount of the inhibitor of MSR1 reduces inflammation, reduces demyelination, reduces axonal loss and/or reduces neuronal loss in the mammal.

T. The method of any one of the preceding embodiments, wherein the conditions effective to inhibit an autoimmune or inflammatory disease comprise administering the inhibitor of MSR1 at dosing intervals effective for treating the disease or inhibiting the onset of the disease.

U. The method of any one the preceding embodiments, wherein the inhibitor is administered once, twice or three times per day.

V. The method of any of embodiments A-T, wherein the inhibitor is administered once, twice or three times per week, or once, twice or three times per month.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed:

1. A method of treating an autoimmune or inflammatory disease in a mammal comprising: administering to a mammal in need thereof an anti-MSR1 antibody, or a fragment thereof, selective for an MSR1 antigenic peptide selected from the group consisting of SEQ ID NOs:6, 7, 8, and 9 that inhibits MSR1 protein under conditions effective to inhibit an autoimmune or inflammatory disease macrophage infiltration.

2. The method of claim 1, wherein the anti-MSR1 antibody, or a fragment thereof, is a Fab or F(ab)$_2$ fragment of an anti-MSR1 antibody, or antibody fragments thereof, and combinations thereof.

3. The method of claim 2, wherein the antibody is a monoclonal antibody; or the antibody fragment, the Fab fragment or the F(ab)$_2$ fragment is from a monoclonal antibody.

4. The method of claim 2, wherein the antibody is a polyclonal antibody; or the antibody fragment, the Fab fragment or the F(ab)$_2$ fragment is from a polyclonal antibody preparation.

5. The method of claim 2, wherein the antibody, the antibody fragment, the Fab fragment or the F(ab)$_2$ fragment is from a recombinant antibody library.

6. The method of claim 2, wherein the antibody, the antibody fragment, the Fab fragment or the F(ab)$_2$ fragment is expressed in eukaryotic cells.

7. The method of claim 2, wherein the antibody, the antibody fragment, the Fab fragment or the F(ab)$_2$ fragment is expressed in prokaryotic cells.

8. The method of claim 2, wherein the antibody, the antibody fragment, the Fab fragment or the F(ab)$_2$ fragment is generated through an in vitro technique.

9. The method of claim 8, wherein the in vitro technique comprises use of a library of antibodies, antibody fragments, Fab fragments or F(ab)$_2$ fragments, where the antibodies, antibody fragments, Fab fragments or the F(ab)$_2$ fragment are displayed on phage, cells or ribosomes.

10. The method of claim 2, wherein the antibody, antibody fragment, Fab fragment, or F(ab)$_2$ fragment binds to a polypeptide or a peptide comprising of SEQ ID NOs:6, 7, 8, or 9.

11. The method of claim 1, wherein the mammal is human.

12. The method of claim 1, wherein the disease is an autoimmune disease.

13. The method of claim 1, wherein the disease is an autoimmune demyelinating neuropathy.

14. The method of claim 13, wherein the autoimmune demyelinating neuropathy is chronic inflammatory demyelinating polyneuropathy (CIDP) or Guillain-Barre syndrome (GBS).

15. The method of claim 1, wherein the disease is an inflammatory disease.

16. The method of claim 1, wherein the anti-MSR1 antibody, or a fragment thereof, deactivates previously activated macrophages, inhibits macrophage activation, inhibits macrophage interactions, inhibits antigen presentation, and/or inhibits extracellular adhesion in the mammal.

17. The method of claim 1, wherein the conditions effective to inhibit an autoimmune or inflammatory disease comprise administering a therapeutically effective amount of the anti-MSR1 antibody, or a fragment thereof.

18. The method of claim 17, wherein the therapeutically effective amount of the anti-MSR1 antibody, or a fragment thereof deactivates previously activated macrophages, inhibits macrophage activation, inhibits macrophage interactions, inhibits antigen presentation or inhibits extracellular adhesion.

19. The method of claim 17, wherein the therapeutically effective amount of the anti-MSR1 antibody, or a fragment thereof reduces inflammation, reduces demyelination, reduces axonal loss and/or reduces neuronal loss in the mammal.

20. The method of claim 1, wherein the conditions effective to inhibit an autoimmune or inflammatory disease comprise administering the anti-MSR1 antibody, or a fragment thereof at dosing intervals effective for treating the disease or inhibiting the onset of the disease.

21. The method of claim 1, wherein the anti-MSR1 antibody, or a fragment thereof is administered once, twice or three times per day.

22. The method of claim 1, wherein the anti-MSR1 antibody, or a fragment thereof, is administered once, twice or three times per week, or once, twice or three times per month.

23. The method of claim 1, wherein the autoimmune or inflammatory disease is polymyositis, dermatomyositis, stroke, scleroderma, acute coronary syndrome, Alzheimer's disease, or an autoimmune diseases of the vascular system.

24. The method of claim, wherein the anti-MSR1 antibody, or fragment thereof, binds to MSR1 on human macrophages.

25. The method of claim 1, wherein the autoimmune or inflammatory disease is demyelinating neuropathy, autoimmune disease of the brain, an autoimmune disease of the muscle, an autoimmune disease of the gastro-intestinal tract, autoimmune disease of the renal system, an autoimmune diseases of joints, an autoimmune disease of skin, an autoimmune disease of the pulmonary system, an autoimmune disease of the endocrine system, or an autoimmune disease of the hematopoietic system.

\* \* \* \* \*

SEQUENCE LISTING

```
<160> NUMBER OF SEQ ID NOS: 13

<210> SEQ ID NO 1
<211> LENGTH: 451
<212> TYPE: PRT
<213> ORGANISM: Homo sapien

<400> SEQUENCE: 1

Met Gln Trp Asp His Phe His Asn Gln Gln Glu Asp Thr Asp Ser
1               5                   10                  15

Cys Ser Glu Ser Val Lys Phe Asp Ala Arg Ser Met Thr Ala Leu Leu
            20                  25                  30

Pro Pro Asn Pro Lys Asn Ser Pro Ser Leu Gln Glu Lys Leu Lys Ser
        35                  40                  45
```

```
Phe Lys Ala Ala Leu Ile Ala Leu Tyr Leu Leu Val Phe Ala Val Leu
    50                  55                  60

Ile Pro Leu Ile Gly Ile Val Ala Ala Gln Leu Leu Lys Trp Glu Thr
65                  70                  75                  80

Lys Asn Cys Ser Val Ser Ser Thr Asn Ala Asn Asp Ile Thr Gln Ser
                85                  90                  95

Leu Thr Gly Lys Gly Asn Asp Ser Glu Glu Met Arg Phe Gln Glu
                100                 105                 110

Val Phe Met Glu His Met Ser Asn Met Glu Lys Arg Ile Gln His Ile
            115                 120                 125

Leu Asp Met Glu Ala Asn Leu Met Asp Thr Glu His Phe Gln Asn Phe
    130                 135                 140

Ser Met Thr Thr Asp Gln Arg Phe Asn Asp Ile Leu Leu Gln Leu Ser
145                 150                 155                 160

Thr Leu Phe Ser Ser Val Gln Gly His Gly Asn Ala Ile Asp Glu Ile
                165                 170                 175

Ser Lys Ser Leu Ile Ser Leu Asn Thr Thr Leu Leu Asp Leu Gln Leu
            180                 185                 190

Asn Ile Glu Asn Leu Asn Gly Lys Ile Gln Glu Asn Thr Phe Lys Gln
                195                 200                 205

Gln Glu Glu Ile Ser Lys Leu Glu Glu Arg Val Tyr Asn Val Ser Ala
        210                 215                 220

Glu Ile Met Ala Met Lys Glu Glu Gln Val His Leu Glu Gln Glu Ile
225                 230                 235                 240

Lys Gly Glu Val Lys Val Leu Asn Asn Ile Thr Asn Asp Leu Arg Leu
                245                 250                 255

Lys Asp Trp Glu His Ser Gln Thr Leu Arg Asn Ile Thr Leu Ile Gln
            260                 265                 270

Gly Pro Pro Gly Pro Pro Gly Glu Lys Gly Asp Arg Gly Pro Thr Gly
        275                 280                 285

Glu Ser Gly Pro Arg Gly Phe Pro Gly Pro Ile Gly Pro Pro Gly Leu
    290                 295                 300

Lys Gly Asp Arg Gly Ala Ile Gly Phe Pro Gly Ser Arg Gly Leu Pro
305                 310                 315                 320

Gly Tyr Ala Gly Arg Pro Gly Asn Ser Gly Pro Lys Gly Gln Lys Gly
                325                 330                 335

Glu Lys Gly Ser Gly Asn Thr Leu Thr Pro Phe Thr Lys Val Arg Leu
            340                 345                 350

Val Gly Gly Ser Gly Pro His Glu Gly Arg Val Glu Ile Leu His Ser
        355                 360                 365

Gly Gln Trp Gly Thr Ile Cys Asp Asp Arg Trp Glu Val Arg Val Gly
    370                 375                 380

Gln Val Val Cys Arg Ser Leu Gly Tyr Pro Gly Val Gln Ala Val His
385                 390                 395                 400

Lys Ala Ala His Phe Gly Gln Gly Thr Gly Pro Ile Trp Leu Asn Glu
                405                 410                 415

Val Phe Cys Phe Gly Arg Glu Ser Ser Ile Glu Glu Cys Lys Ile Arg
            420                 425                 430

Gln Trp Gly Thr Arg Ala Cys Ser His Ser Glu Asp Ala Gly Val Thr
        435                 440                 445

Cys Thr Leu
450
```

```
<210> SEQ ID NO 2
<211> LENGTH: 375
<212> TYPE: PRT
<213> ORGANISM: Homo sapien

<400> SEQUENCE: 2

Lys Trp Glu Thr Lys Asn Cys Ser Val Ser Thr Asn Ala Asn Asp
 1               5                  10                  15

Ile Thr Gln Ser Leu Thr Gly Lys Gly Asn Asp Ser Glu Glu Met
            20                  25                  30

Arg Phe Gln Glu Val Phe Met Glu His Met Ser Asn Met Glu Lys Arg
            35                  40                  45

Ile Gln His Ile Leu Asp Met Glu Ala Asn Leu Met Asp Thr Glu His
50                  55                  60

Phe Gln Asn Phe Ser Met Thr Thr Asp Gln Arg Phe Asn Asp Ile Leu
65                  70                  75                  80

Leu Gln Leu Ser Thr Leu Phe Ser Ser Val Gln Gly His Gly Asn Ala
                85                  90                  95

Ile Asp Glu Ile Ser Lys Ser Leu Ile Ser Leu Asn Thr Thr Leu Leu
            100                 105                 110

Asp Leu Gln Leu Asn Ile Glu Asn Leu Asn Gly Lys Ile Gln Glu Asn
            115                 120                 125

Thr Phe Lys Gln Gln Glu Glu Ile Ser Lys Leu Glu Glu Arg Val Tyr
130                 135                 140

Asn Val Ser Ala Glu Ile Met Ala Met Lys Glu Gln Val His Leu
145                 150                 155                 160

Glu Gln Glu Ile Lys Gly Glu Val Lys Val Leu Asn Asn Ile Thr Asn
                165                 170                 175

Asp Leu Arg Leu Lys Asp Trp Glu His Ser Gln Thr Leu Arg Asn Ile
            180                 185                 190

Thr Leu Ile Gln Gly Pro Pro Gly Pro Pro Gly Glu Lys Gly Asp Arg
            195                 200                 205

Gly Pro Thr Gly Glu Ser Gly Pro Arg Gly Phe Pro Gly Pro Ile Gly
210                 215                 220

Pro Pro Gly Leu Lys Gly Asp Arg Gly Ala Ile Gly Phe Pro Gly Ser
225                 230                 235                 240

Arg Gly Leu Pro Gly Tyr Ala Gly Arg Pro Gly Asn Ser Gly Pro Lys
                245                 250                 255

Gly Gln Lys Gly Glu Lys Gly Ser Gly Asn Thr Leu Thr Pro Phe Thr
            260                 265                 270

Lys Val Arg Leu Val Gly Gly Ser Gly Pro His Glu Gly Arg Val Glu
            275                 280                 285

Ile Leu His Ser Gly Gln Trp Gly Thr Ile Cys Asp Asp Arg Trp Glu
290                 295                 300

Val Arg Val Gly Gln Val Val Cys Arg Ser Leu Gly Tyr Pro Gly Val
305                 310                 315                 320

Gln Ala Val His Lys Ala Ala His Phe Gly Gln Gly Thr Gly Pro Ile
                325                 330                 335

Trp Leu Asn Glu Val Phe Cys Phe Gly Arg Glu Ser Ser Ile Glu Glu
            340                 345                 350

Cys Lys Ile Arg Gln Trp Gly Thr Arg Ala Cys Ser His Ser Glu Asp
            355                 360                 365

Ala Gly Val Thr Cys Thr Leu
370                 375
```

<210> SEQ ID NO 3
<211> LENGTH: 451
<212> TYPE: PRT
<213> ORGANISM: Homo sapien

<400> SEQUENCE: 3

Met Glu Gln Trp Asp His Phe His Asn Gln Glu Asp Thr Asp Ser
 1               5                  10                  15

Cys Ser Glu Ser Val Lys Phe Asp Ala Arg Ser Met Thr Ala Leu Leu
            20                  25                  30

Pro Pro Asn Pro Lys Asn Ser Pro Ser Leu Gln Glu Lys Leu Lys Ser
                35                  40                  45

Phe Lys Ala Ala Leu Ile Ala Leu Tyr Leu Leu Val Phe Ala Val Leu
 50                  55                  60

Ile Pro Leu Ile Gly Ile Val Ala Ala Gln Leu Leu Lys Trp Glu Thr
 65                  70                  75                  80

Lys Asn Cys Ser Val Ser Ser Thr Asn Ala Asn Asp Ile Thr Gln Ser
                85                  90                  95

Leu Thr Gly Lys Gly Asn Asp Ser Glu Glu Met Arg Phe Gln Glu
                100                 105                 110

Val Phe Met Glu His Met Ser Asn Met Glu Lys Arg Ile Gln His Ile
            115                 120                 125

Leu Asp Met Glu Ala Asn Leu Met Asp Thr Glu His Phe Gln Asn Phe
130                 135                 140

Ser Met Thr Thr Asp Gln Arg Phe Asn Asp Ile Leu Leu Gln Leu Ser
145                 150                 155                 160

Thr Leu Phe Ser Ser Val Gln Gly His Gly Asn Ala Ile Asp Glu Ile
                165                 170                 175

Ser Lys Ser Leu Ile Ser Leu Asn Thr Thr Leu Leu Asp Leu Gln Leu
                180                 185                 190

Asn Ile Glu Asn Leu Asn Gly Lys Ile Gln Glu Asn Thr Phe Lys Gln
            195                 200                 205

Gln Glu Glu Ile Ser Lys Leu Glu Glu Arg Val Tyr Asn Val Ser Ala
        210                 215                 220

Glu Ile Met Ala Met Lys Glu Glu Gln Val His Leu Glu Gln Glu Ile
225                 230                 235                 240

Lys Gly Glu Val Lys Val Leu Asn Asn Ile Thr Asn Asp Leu Arg Leu
                245                 250                 255

Lys Asp Trp Glu His Ser Gln Thr Leu Arg Asn Ile Thr Leu Ile Gln
                260                 265                 270

Gly Pro Pro Gly Pro Gly Glu Lys Gly Asp Arg Gly Pro Thr Gly
            275                 280                 285

Glu Ser Gly Pro Arg Gly Phe Pro Gly Pro Ile Gly Pro Pro Gly Leu
        290                 295                 300

Lys Gly Asp Arg Gly Ala Ile Gly Phe Pro Gly Ser Arg Gly Leu Pro
305                 310                 315                 320

Gly Tyr Ala Gly Arg Pro Gly Asn Ser Gly Pro Lys Gly Gln Lys Gly
                325                 330                 335

Glu Lys Gly Ser Gly Asn Thr Leu Thr Pro Phe Thr Lys Val Arg Leu
            340                 345                 350

Val Gly Gly Ser Gly Pro His Glu Gly Arg Val Glu Ile Leu His Ser
        355                 360                 365

Gly Gln Trp Gly Thr Ile Cys Asp Asp Arg Trp Glu Val Arg Val Gly
370                 375                 380

```
Gln Val Val Cys Arg Ser Leu Gly Tyr Pro Gly Val Gln Ala Val His
385                 390                 395                 400

Lys Ala Ala His Phe Gly Gln Gly Thr Gly Pro Ile Trp Leu Asn Glu
            405                 410                 415

Val Phe Cys Phe Gly Arg Glu Ser Ser Ile Glu Glu Cys Lys Ile Arg
            420                 425                 430

Gln Trp Gly Thr Arg Ala Cys Ser His Ser Glu Asp Ala Gly Val Thr
            435                 440                 445

Cys Thr Leu
        450

<210> SEQ ID NO 4
<211> LENGTH: 358
<212> TYPE: PRT
<213> ORGANISM: Homo sapien

<400> SEQUENCE: 4

Met Glu Gln Trp Asp His Phe His Asn Gln Gln Glu Asp Thr Asp Ser
 1               5                  10                  15

Cys Ser Glu Ser Val Lys Phe Asp Ala Arg Ser Met Thr Ala Leu Leu
            20                  25                  30

Pro Pro Asn Pro Lys Asn Ser Pro Ser Leu Gln Glu Lys Leu Lys Ser
            35                  40                  45

Phe Lys Ala Ala Leu Ile Ala Leu Tyr Leu Leu Val Phe Ala Val Leu
 50                  55                  60

Ile Pro Leu Ile Gly Ile Val Ala Ala Gln Leu Leu Lys Trp Glu Thr
 65                  70                  75                  80

Lys Asn Cys Ser Val Ser Ser Thr Asn Ala Asn Asp Ile Thr Gln Ser
            85                  90                  95

Leu Thr Gly Lys Gly Asn Asp Ser Glu Glu Met Arg Phe Gln Glu
            100                 105                 110

Val Phe Met Glu His Met Ser Asn Met Glu Lys Arg Ile Gln His Ile
            115                 120                 125

Leu Asp Met Glu Ala Asn Leu Met Asp Thr Glu His Phe Gln Asn Phe
130                 135                 140

Ser Met Thr Thr Asp Gln Arg Phe Asn Asp Ile Leu Leu Gln Leu Ser
145                 150                 155                 160

Thr Leu Phe Ser Ser Val Gln Gly His Gly Asn Ala Ile Asp Glu Ile
            165                 170                 175

Ser Lys Ser Leu Ile Ser Leu Asn Thr Thr Leu Leu Asp Leu Gln Leu
            180                 185                 190

Asn Ile Glu Asn Leu Asn Gly Lys Ile Gln Glu Asn Thr Phe Lys Gln
            195                 200                 205

Gln Glu Glu Ile Ser Lys Leu Glu Glu Arg Val Tyr Asn Val Ser Ala
        210                 215                 220

Glu Ile Met Ala Met Lys Glu Glu Gln Val His Leu Glu Gln Glu Ile
225                 230                 235                 240

Lys Gly Glu Val Lys Val Leu Asn Asn Ile Thr Asn Asp Leu Arg Leu
            245                 250                 255

Lys Asp Trp Glu His Ser Gln Thr Leu Arg Asn Ile Thr Leu Ile Gln
            260                 265                 270

Gly Pro Pro Gly Pro Pro Gly Glu Lys Gly Asp Arg Gly Pro Thr Gly
            275                 280                 285

Glu Ser Gly Pro Arg Gly Phe Pro Gly Pro Ile Gly Pro Pro Gly Leu
```

```
            290                 295                 300
Lys Gly Asp Arg Gly Ala Ile Gly Phe Pro Gly Ser Arg Gly Leu Pro
305                 310                 315                 320

Gly Tyr Ala Gly Arg Pro Gly Asn Ser Gly Pro Lys Gly Gln Lys Gly
                325                 330                 335

Glu Lys Gly Ser Gly Asn Thr Leu Arg Pro Val Gln Leu Thr Asp His
            340                 345                 350

Ile Arg Ala Gly Pro Ser
        355

<210> SEQ ID NO 5
<211> LENGTH: 458
<212> TYPE: PRT
<213> ORGANISM: Mus musculus

<400> SEQUENCE: 5

Met Thr Lys Glu Met Thr Glu Asn Gln Arg Leu Cys Pro His Glu Gln
1               5                   10                  15

Glu Asp Ala Asp Cys Ser Ser Glu Ser Val Lys Phe Asp Ala Arg Ser
            20                  25                  30

Met Thr Ala Ser Leu Pro His Ser Thr Lys Asn Gly Pro Ser Leu Gln
        35                  40                  45

Glu Lys Leu Lys Ser Phe Lys Ala Ala Leu Ile Ala Leu Tyr Leu Leu
    50                  55                  60

Val Phe Ala Val Leu Ile Pro Val Val Gly Ile Val Thr Ala Gln Leu
65                  70                  75                  80

Leu Asn Trp Glu Met Lys Asn Cys Leu Val Cys Ser Leu Asn Thr Ser
                85                  90                  95

Asp Thr Ser Gln Gly Pro Met Glu Lys Glu Asn Thr Ser Lys Val Glu
            100                 105                 110

Met Arg Phe Thr Ile Ile Met Glu His Met Lys Asp Met Glu Glu Arg
        115                 120                 125

Ile Glu Ser Ile Ser Asn Ser Lys Ala Asp Leu Ile Asp Thr Glu Arg
    130                 135                 140

Phe Gln Asn Phe Ser Met Ala Thr Asp Gln Arg Leu Asn Asp Ile Leu
145                 150                 155                 160

Leu Gln Leu Asn Ser Leu Ile Ser Ser Val Gln Glu His Gly Asn Ser
                165                 170                 175

Leu Asp Ala Ile Ser Lys Ser Leu Gln Ser Leu Asn Met Thr Leu Leu
            180                 185                 190

Asp Val Gln Leu His Thr Glu Thr Leu Asn Val Arg Val Arg Glu Ser
        195                 200                 205

Thr Ala Lys Gln Gln Glu Asp Ile Ser Lys Leu Glu Glu Arg Val Tyr
    210                 215                 220

Lys Val Ser Ala Glu Val Gln Ser Val Lys Glu Glu Gln Ala His Val
225                 230                 235                 240

Glu Gln Glu Val Lys Gln Glu Val Arg Val Leu Asn Asn Ile Thr Asn
                245                 250                 255

Asp Leu Arg Leu Lys Asp Trp Glu His Ser Gln Thr Leu Lys Asn Ile
            260                 265                 270

Thr Phe Ile Gln Gly Pro Pro Gly Pro Gln Gly Glu Lys Gly Asp Arg
        275                 280                 285

Gly Leu Thr Gly Gln Thr Gly Pro Pro Gly Ala Pro Gly Ile Arg Gly
    290                 295                 300
```

```
Ile Pro Gly Val Lys Gly Asp Arg Gly Gln Ile Gly Phe Pro Gly Gly
305                 310                 315                 320

Arg Gly Asn Pro Gly Ala Pro Gly Lys Pro Gly Arg Ser Gly Ser Pro
            325                 330                 335

Gly Pro Lys Gly Gln Lys Gly Glu Lys Gly Ser Val Gly Gly Ser Thr
            340                 345                 350

Pro Leu Lys Thr Val Arg Leu Val Gly Ser Gly Ala His Glu Gly
            355                 360                 365

Arg Val Glu Ile Phe His Gln Gly Gln Trp Gly Thr Ile Cys Asp Asp
370                 375                 380

Arg Trp Asp Ile Arg Ala Gly Gln Val Val Cys Arg Ser Leu Gly Tyr
385                 390                 395                 400

Gln Glu Val Leu Ala Val His Lys Arg Ala His Phe Gly Gln Gly Thr
            405                 410                 415

Gly Pro Ile Trp Leu Asn Glu Val Met Cys Phe Gly Arg Glu Ser Ser
            420                 425                 430

Ile Glu Asn Cys Lys Ile Asn Gln Trp Gly Val Leu Ser Cys Ser His
            435                 440                 445

Ser Glu Asp Ala Gly Val Thr Cys Thr Ser
450                 455

<210> SEQ ID NO 6
<211> LENGTH: 18
<212> TYPE: PRT
<213> ORGANISM: Rattus norvegicus

<400> SEQUENCE: 6

Arg Ser Gly Phe Pro Gly Pro Lys Gly Gln Lys Gly Glu Lys Gly Arg
1               5                   10                  15

Ala Gly

<210> SEQ ID NO 7
<211> LENGTH: 18
<212> TYPE: PRT
<213> ORGANISM: Homo sapien

<400> SEQUENCE: 7

Arg Pro Gly Asn Ser Gly Pro Lys Gly Gln Lys Gly Glu Lys Gly Ser
1               5                   10                  15

Gly Asn

<210> SEQ ID NO 8
<211> LENGTH: 18
<212> TYPE: PRT
<213> ORGANISM: Homo sapien

<400> SEQUENCE: 8

Arg Pro Gly Asn Ser Gly Pro Lys Gly Gln Lys Gly Glu Lys Gly Ser
1               5                   10                  15

Gly Asn

<210> SEQ ID NO 9
<211> LENGTH: 18
<212> TYPE: PRT
<213> ORGANISM: Mus musculus

<400> SEQUENCE: 9

Arg Ser Gly Ser Pro Gly Pro Lys Gly Gln Lys Gly Glu Lys Gly Ser
1               5                   10                  15
```

```
Val Gly

<210> SEQ ID NO 10
<211> LENGTH: 14
<212> TYPE: PRT
<213> ORGANISM: Rattus norvegicus

<400> SEQUENCE: 10

Lys Asn Lys Glu His Gln Lys Pro Thr Gly Pro Pro Ala Lys
1               5                   10

<210> SEQ ID NO 11
<211> LENGTH: 26
<212> TYPE: PRT
<213> ORGANISM: Rattus norvegicus

<400> SEQUENCE: 11

Thr Glu Ser Pro Phe Lys Asn Thr Glu Ile Ser Phe Lys Leu Gly Gln
1               5                   10                  15

Glu Phe Glu Glu Thr Thr Ala Asp Asn Arg
            20                  25

<210> SEQ ID NO 12
<211> LENGTH: 26
<212> TYPE: PRT
<213> ORGANISM: Rattus norvegicus

<400> SEQUENCE: 12

Thr Glu Ser Pro Phe Lys Asn Thr Glu Ile Ser Phe Lys Leu Gly Gln
1               5                   10                  15

Glu Phe Glu Glu Thr Thr Ala Asp Asn Arg
            20                  25

<210> SEQ ID NO 13
<211> LENGTH: 5
<212> TYPE: PRT
<213> ORGANISM: Artificial Sequence
<220> FEATURE:
<223> OTHER INFORMATION: A synthetic peptide

<400> SEQUENCE: 13

Gly Gly Gly Gly Ser
1               5
```